(12) United States Patent
McCullen

(10) Patent No.: US 11,382,758 B2
(45) Date of Patent: Jul. 12, 2022

(54) IMPLANTABLE DEVICES FOR MUSCULOSKELETAL REPAIR AND REGENERATION

(71) Applicant: Seth McCullen, Greenville, SC (US)

(72) Inventor: Seth McCullen, Greenville, SC (US)

( * ) Notice: Subject to any disclaimer, the term of this patent is extended or adjusted under 35 U.S.C. 154(b) by 330 days.

(21) Appl. No.: 16/567,632

(22) Filed: Sep. 11, 2019

(65) Prior Publication Data

US 2020/0000599 A1   Jan. 2, 2020

Related U.S. Application Data

(63) Continuation of application No. 15/975,151, filed on May 9, 2018, now Pat. No. 10,449,053, which is a
(Continued)

(51) Int. Cl.
*A61F 2/38* (2006.01)
*A61F 2/30* (2006.01)
*A61F 2/44* (2006.01)

(52) U.S. Cl.
CPC ........ *A61F 2/3872* (2013.01); *A61F 2/30756* (2013.01); *A61F 2002/30009* (2013.01);
(Continued)

(58) Field of Classification Search
CPC ............ A61F 2/3872; A61F 2002/0068; A61F 2/0063; A61F 2002/30009;
(Continued)

(56) References Cited

U.S. PATENT DOCUMENTS 3,867,728 A * 2/1975 Stubstad .................. A61F 2/441
623/17.16
4,195,368 A   4/1980 Patrichi
(Continued)

FOREIGN PATENT DOCUMENTS

EP   0 372 811 B1   6/1990
EP   3 269 335 A1   1/2018
(Continued)

OTHER PUBLICATIONS

Extended European Search Report for European Patent Application No. 15847098.9, dated May 16, 2018 (7 pages).
(Continued)

*Primary Examiner* — Alvin J Stewart
(74) *Attorney, Agent, or Firm* — Thrive IP®; Jeremy M. Stipkala

(57) ABSTRACT

This application describes an implantable device for tissue repair comprising at least two fabrics with interconnecting spacer elements transversing, connecting, and separating the fabrics, forming the device. Some embodiments have fixation points which can be an extension of at least one of the fabrics. The implantable device allows modification of the two fabrics having varying constructions, chemistries, and physical properties. The spacer elements create a space between the two fabrics, which can be used for the loading of biological materials (peptides, proteins, cells, tissues), offer compression resistance (i.e. stiffness), and compression recovery (i.e., return to original dimensions) following deformation and removal of deforming load. The inclusive fixation points of the fabrics are designed to allow for fine adjustment of the sizing and tension of the device to promote integration with the surrounding tissues as well as maximize the compressive resistance. The fixation points can include either the first fabric, the second fabric, or the combination of both fabrics. This device is suitable for soft and hard tissue regeneration or replacement with a preference for musculoskeletal tissues including but not limited to cartilage (including hyaline (referred to as articular; e.g. cartilage on the ends of long bones), fibrous (e.g. meniscus or intervertebral discs), elastic (e.g. ear, epiglottis)), bone, muscle, tendon, ligament, and fat.

20 Claims, 12 Drawing Sheets

Related U.S. Application Data continuation of application No. 15/293,319, filed on Oct. 14, 2016, now Pat. No. 9,993,346, which is a continuation of application No. 14/432,261, filed as application No. PCT/US2013/062809 on Oct. 1, 2013, now Pat. No. 9,498,335.

(60) Provisional application No. 61/708,917, filed on Oct. 2, 2012.

(52) U.S. Cl.
CPC ............ *A61F 2002/30576* (2013.01); *A61F 2002/30677* (2013.01); *A61F 2002/30757* (2013.01); *A61F 2002/30766* (2013.01); *A61F 2002/30971* (2013.01); *A61F 2002/4495* (2013.01); *A61F 2240/001* (2013.01)

(58) Field of Classification Search
CPC .. A61F 2002/30546; A61F 2002/30563; A61F 2002/30576; A61F 2002/30028; A61F 2002/30011; A61F 2002/30014; A61F 2002/30767; A61F 2002/30766; A61F 2/30756; A61F 2002/30757; A61F 2002/30759; A61F 27/3869; A61F 27/3891; A61F 27/60; A61F 2/105; A61F 2002/30004; A61F 2210/0076; A61F 2250/0028; A61F 2250/0051; A61F 2250/0052

See application file for complete search history.

(56) References Cited

U.S. PATENT DOCUMENTS

| | | | |
|---|---|---|---|
| 4,344,193 A | 8/1982 | Kenny | |
| 4,502,161 A | 3/1985 | Wall | |
| 4,668,233 A | 5/1987 | Seedhom et al. | |
| 4,919,667 A * | 4/1990 | Richmond | A61F 2/3872 623/14.12 |
| 4,919,677 A | 4/1990 | Richmond | |
| 5,116,357 A | 5/1992 | Eberbach | |
| 5,254,133 A | 10/1993 | Seid | |
| 6,093,205 A | 7/2000 | McLeod et al. | |
| 6,113,623 A * | 9/2000 | Sgro | A61B 17/0057 606/151 |
| 6,113,640 A | 9/2000 | Tormala et al. | |
| 6,645,211 B2 | 11/2003 | Magana | |
| 6,679,914 B1 | 1/2004 | Gabbay | |
| 6,730,252 B1 | 5/2004 | Teoh et al. | |
| 6,736,854 B2 | 5/2004 | Vadurro et al. | |
| 6,746,485 B1 | 6/2004 | Zucherman et al. | |
| 6,755,867 B2 | 6/2004 | Rousseau | |
| 6,783,546 B2 | 8/2004 | Zucherman et al. | |
| 7,153,325 B2 | 12/2006 | Kim et al. | |
| 7,163,563 B2 | 1/2007 | Schwartz et al. | |
| 7,192,604 B2 | 3/2007 | Brown et al. | |
| 7,297,161 B2 | 11/2007 | Fell | |
| 7,341,602 B2 | 3/2008 | Fell | |
| 7,429,270 B2 | 9/2008 | Baumgartner | |
| 7,476,250 B1 | 1/2009 | Mansmann | |
| 7,572,291 B2 | 8/2009 | Gil et al. | |
| 7,758,643 B2 | 7/2010 | Stone et al. | |
| 7,871,440 B2 * | 1/2011 | Schwartz | A61F 2/3872 623/14.12 |
| 7,905,922 B2 | 3/2011 | Bergeron | |
| 7,976,578 B2 | 7/2011 | Marvel | |
| 8,092,529 B2 | 1/2012 | Malaviya | |
| 8,114,156 B2 | 2/2012 | Hatch | |
| 8,282,681 B2 | 10/2012 | McLeod et al. | |
| 8,287,594 B2 | 10/2012 | Cragg | |
| 8,292,954 B2 | 10/2012 | Robinson | |
| 8,298,290 B2 | 10/2012 | Pelissier et al. | |
| 8,357,203 B2 | 1/2013 | White | |
| 8,361,147 B2 | 1/2013 | Shterling | |
| 8,403,985 B2 | 3/2013 | Hodorek | |
| 8,623,085 B2 * | 1/2014 | Gatt | A61F 2/3094 623/14.12 |
| 8,690,919 B2 | 4/2014 | Lange et al. | |
| 8,858,632 B2 | 10/2014 | Mansmann et al. | |
| 8,968,419 B2 | 3/2015 | Calvez et al. | |
| 9,005,308 B2 | 4/2015 | Stopek et al. | |
| 9,044,278 B2 | 6/2015 | Tanaka | |
| 9,119,698 B2 | 9/2015 | Caneiro et al. | |
| 9,211,362 B2 | 12/2015 | Hwang et al. | |
| 9,498,335 B2 | 11/2016 | McCullen | |
| 9,993,346 B2 | 6/2018 | McCullen | |
| 10,022,230 B2 | 7/2018 | Amis | |
| 10,034,755 B2 * | 7/2018 | McCullen | A61F 2/30767 |
| 10,449,053 B2 | 10/2019 | McCullen | |
| 10,543,092 B1 * | 1/2020 | Huang | A61L 27/3852 |
| 10,743,998 B2 * | 8/2020 | McCullen | A61F 2/30767 |
| 10,765,521 B2 * | 9/2020 | van Donkelaar | A61F 2/30756 |
| 2002/0022884 A1 | 2/2002 | Mansmann | |
| 2002/0173855 A1 * | 11/2002 | Mansmann | A61F 2/30756 623/23.72 |
| 2003/0012805 A1 * | 1/2003 | Chen | A61L 27/48 424/423 |
| 2003/0036797 A1 | 2/2003 | Malaviya et al. | |
| 2003/0114552 A1 | 6/2003 | Schacht | |
| 2003/0135209 A1 | 7/2003 | Seedhom et al. | |
| 2004/0059416 A1 | 3/2004 | Murray et al. | |
| 2004/0133275 A1 * | 7/2004 | Mansmann | A61F 2/30965 623/14.12 |
| 2004/0143344 A1 | 7/2004 | Malaviya et al. | |
| 2004/0266000 A1 | 12/2004 | Offermann et al. | |
| 2004/0267362 A1 | 12/2004 | Hwang et al. | |
| 2005/0027364 A1 * | 2/2005 | Kim | A61F 2/4611 623/17.13 |
| 2006/0052872 A1 * | 3/2006 | Studer | A61F 2/4425 623/17.13 |
| 2006/0085080 A1 * | 4/2006 | Bechgaard | B32B 27/12 623/23.43 |
| 2006/0241756 A1 | 10/2006 | Fritz et al. | |
| 2007/0073394 A1 | 3/2007 | Seedhom et al. | |
| 2007/0100450 A1 | 5/2007 | Hodorek | |
| 2007/0150063 A1 * | 6/2007 | Ruberte | A61F 2/442 623/17.16 |
| 2007/0179607 A1 * | 8/2007 | Hodorek | A61F 2/30965 623/14.12 |
| 2007/0239277 A1 | 10/2007 | Beger et al. | |
| 2007/0244484 A1 * | 10/2007 | Luginbuehl | A61F 2/30965 606/86 R |
| 2007/0276506 A1 * | 11/2007 | Troxel | A61F 2/28 623/23.63 |
| 2008/0086210 A1 | 4/2008 | Fox | |
| 2008/0113572 A1 * | 5/2008 | Ragaru | A61F 2/105 442/1 |
| 2008/0154370 A1 | 6/2008 | Mathies | |
| 2008/0183292 A1 | 7/2008 | Trieu | |
| 2008/0255665 A1 | 10/2008 | Weissberg | |
| 2009/0087469 A1 | 4/2009 | Zhang et al. | |
| 2009/0132047 A1 | 5/2009 | Mansmann et al. | |
| 2009/0164014 A1 | 6/2009 | Liljensten et al. | |
| 2009/0276057 A1 | 11/2009 | Trabucco et al. | |
| 2010/0151114 A1 * | 6/2010 | Parrott | D06M 10/08 427/2.26 |
| 2010/0222882 A1 | 9/2010 | Badylak et al. | |
| 2010/0331979 A1 * | 12/2010 | McDade | A61L 27/50 623/14.12 |
| 2011/0066243 A1 | 3/2011 | Rivin et al. | |
| 2011/0093073 A1 * | 4/2011 | Gatt | A61F 2/44 623/14.12 |
| 2011/0166494 A1 * | 7/2011 | Calvez | B29C 66/81433 604/8 |
| 2011/0282451 A1 * | 11/2011 | Sporring | A61L 27/48 623/14.12 |
| 2012/0045651 A1 | 2/2012 | Myung et al. | |
| 2012/0232656 A1 | 9/2012 | Gedet et al. | |
| 2012/0330093 A1 * | 12/2012 | Odermatt | A61F 2/0063 600/30 |
| 2013/0030528 A1 | 1/2013 | Chen et al. | |

(56) References Cited

U.S. PATENT DOCUMENTS

| | | | |
|---|---|---|---|
| 2013/0138211 A1 | 5/2013 | Myung et al. | |
| 2013/0172999 A1 | 7/2013 | Kaplan et al. | |
| 2013/0204393 A1* | 8/2013 | Samaniego | A61L 27/3687 623/23.72 |
| 2013/0268074 A1 | 10/2013 | Vowles | |
| 2013/0312897 A1 | 11/2013 | Vowles | |
| 2014/0031933 A1 | 1/2014 | Gatt et al. | |
| 2014/0222149 A1* | 8/2014 | Amis | A61F 2/30756 623/14.12 |
| 2014/0277451 A1 | 9/2014 | Ganz et al. | |
| 2014/0277569 A1 | 9/2014 | Lange | |
| 2014/0309739 A1 | 10/2014 | Badylak et al. | |
| 2015/0238318 A1* | 8/2015 | McCullen | A61F 2/3872 623/14.12 |
| 2016/0228604 A1* | 8/2016 | Mann | A61L 27/52 |
| 2016/0256285 A1 | 9/2016 | Jansen | |
| 2017/0007741 A1* | 1/2017 | D'Lima | A61F 2/3872 |
| 2017/0065422 A1 | 3/2017 | McCullen | |
| 2019/0231534 A1* | 8/2019 | van Donkelaar | A61F 2/30756 |
| 2020/0060834 A1 | 2/2020 | McCullen et al. | |
| 2020/0069434 A1* | 3/2020 | Mimnaugh | A61F 2/30965 |
| 2020/0163752 A1* | 5/2020 | Salas | A61F 2/30756 |
| 2021/0059828 A1 | 3/2021 | McCullen et al. | |
| 2021/0298908 A1* | 9/2021 | Holmes | A61F 2/30771 |

FOREIGN PATENT DOCUMENTS

| | | |
|---|---|---|
| WO | 2012159018 A1 | 11/2012 |
| WO | 2012168715 A1 | 12/2012 |
| WO | 2014055480 A1 | 4/2014 |
| WO | 2016054463 A1 | 4/2016 |
| WO | 2018204440 A2 | 11/2018 |

OTHER PUBLICATIONS

Written Opinion for PCT/US2013/062809, dated Jan. 10, 2014 (16 pages).

International Search Report for PCT/US2013/062809, dated Jan. 10, 2014 (4 pages).

Communication and European Search Report, for European Patent Application No. EP 13844365.0, dated May 2, 2016 (8 pages).

U. Klinge et al., "Modified Mesh for Hernia Repair that is Adapted to the Physiology of the Abdominal Wall," Eur. J. Surg. 164 (1998) 951-960.

T. Forstemann et al., "Forces and deformations of the abdominal wall—A mechanical and geometrical approach to the linea alba," J. Biomechanics 44 (2011) 600-606.

K. Junge et al., "Elasticity of the anterior abdominal wall and impact for reparation of incisional hernias using mesh implants," Hernia 5 (2001) 113-118.

W. S. Cobb et al., "Normal Intraabdominal Pressure in Healthy Adults," J. Surg. Res., 129 (2005) 231-235.

M. Smietanski et al., "Biomechanics of the front abdominal wall as a potential factor leading to recurrence with laparoscopic ventral hernia repair," Surg. Endosc. (Published online Dec. 15, 2011).

A. K. Williamson et al., "Compressive properties and function-composition relationships of developing bovine articular cartilage," J. Orthopaedic Res. 19 (2001) 1113-1121.

A. K. Williamson et al., "Tensile mechanical properties of bovine articular cartilage: variations with growth and relationships to collagen network components," J. Orthopaedic Res., 21 (2003) 872-880.

P. P. Pott et al., "Mechanical Properties of Mesh Materials Used for Hernia Repair and Soft Tissue Augmentation," PLOS One vol. 7, Issue 10 (2012) e46978.

International Search Report and Written Opinion for PCT/US2015/053630, dated Jan. 11, 2016 (12 pages).

International Search Report for PCT/US2018/030567, dated Sep. 7, 2018 (4 pages).

Written Opinion for PCT/US2018/030567, dated Sep. 7, 2018 (12 pages).

European Search Report for European Patent No. EP 17 18 5178, dated Oct. 26, 2017 (2 pages).

Non-Final Office Action in U.S. Appl. No. 16/035,784 dated Aug. 1, 2019 (8 pages).

\* cited by examiner

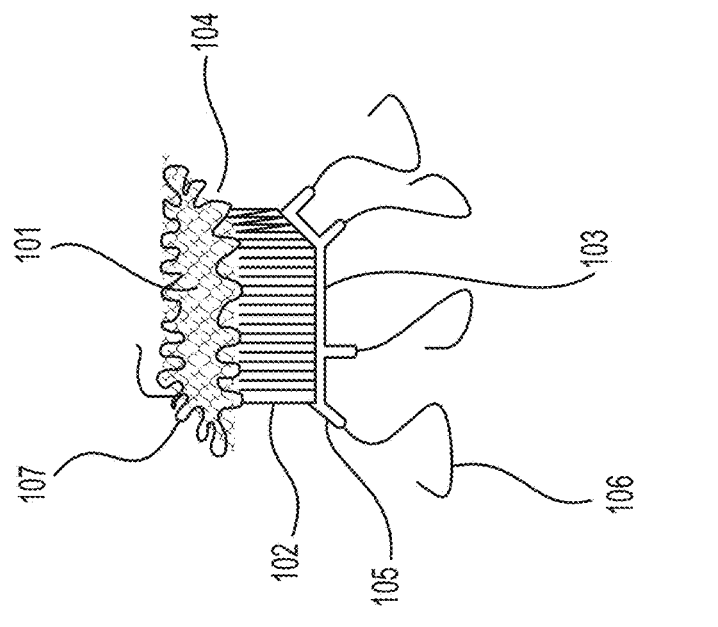
FIG. 1
FIG. 4
FIG. 5
FIG. 6
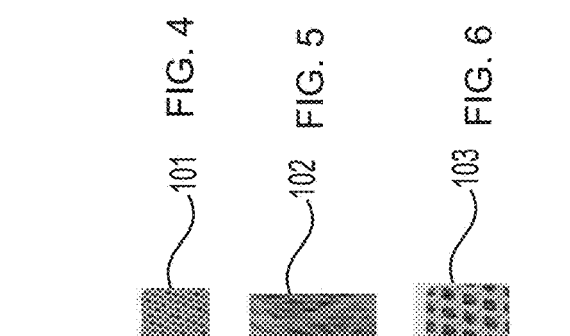
FIG. 3
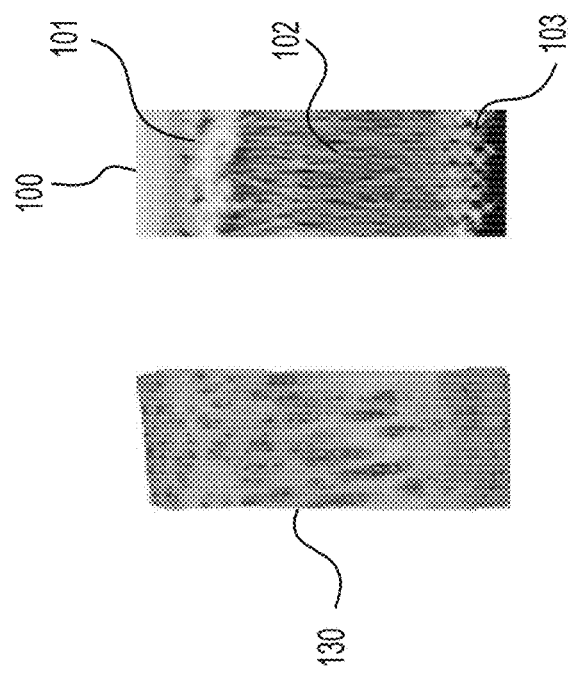
FIG. 2

IMPLANTABLE DEVICES FOR MUSCULOSKELETAL REPAIR AND REGENERATION

CROSS REFERENCE TO RELATED APPLICATIONS

This application is a continuing application of and claims benefit of priority to U.S. Non-Provisional patent application Ser. No. 15/975,151, entitled, "IMPLANTABLE DEVICES FOR MUSCULOSKELETAL REPAIR AND REGENERATION," filed on May 9, 2018, now allowed; which is a continuation of U.S. Non-Provisional patent application Ser. No. 15/293,319, entitled, "IMPLANTABLE DEVICES FOR MUSCULOSKELETAL REPAIR AND REGENERATION," filed on Oct. 14, 2016, which issued as U.S. Pat. No. 9,993,346 B2 on Jun. 12, 2018; which is a continuing application of and claims benefit of priority to U.S. Non-Provisional patent application Ser. No. 14/432,261, entitled, "IMPLANTABLE DEVICES FOR MUSCULOSKELETAL REPAIR AND REGENERATION," filed on Mar. 30, 2015, and which issued as U.S. Pat. No. 9,498,335 B2 on Nov. 22, 2016; which represents the U.S. National Phase of International Patent Application No. PCT/US2013/062809, entitled, "IMPLANTABLE DEVICES FOR MUSCULOSKELETAL REPAIR AND REGENERATION," and filed on Oct. 1, 2013; which in turn claims benefit of priority to U.S. Provisional Patent Application No. 61/708,917, entitled, "IMPLANTABLE DEVICES FOR MUSCULOSKELETAL REPAIR AND REGENERATION," filed on Oct. 2, 2012. The foregoing applications are incorporated herein by reference in their entirety.

BACKGROUND OF INVENTION

Tissue defects resulting from trauma and degeneration are significant challenges in medicine as current tissue replacement technologies are based on end point treatments that do not regenerate the tissue. Musculoskeletal tissues are of significant importance as these tissues support bodily movement, function, and overall human physical activity. When these tissues undergo significant trauma or undergo degeneration due to abnormal use or overuse, they require external intervention to restore normal function. Particular challenges for musculoskeletal injuries include cartilage tissue degeneration. Within the human body there exist three types of cartilage namely elastic, hyaline (articular) and fibrocartilage. Elastic cartilage is the cartilage present in the outer ear, larynx, and epiglottis, while hyaline (articular) and fibrocartilage are found primarily within joints such as the knee. Hyaline or articular cartilage is a type of cartilage found on joint surfaces on the end of long bones. Fibrocartilage consists of fibrous and cartilaginous tissue and is primarily found in within the annulus fibrosus of intervertebral discs, and meniscus of the knee joint. Both articular and fibrocartilage provide a bearing surface that distributes load for force transmission and act as a shock absorber for joints. However both articular and fibrocartilage can undergo degeneration following abnormal loading or overloading in joints such as the knee, resulting in the formation of tears and/or lesions. These deformities are based on the deterioration of the cartilage surface based on a thinning of the cartilage surface due to excessive wear. Unlike other musculoskeletal tissues that are able to undergo some regeneration (i.e. bone) cartilage lacks the intrinsic regenerative capacity for repair based on the tissue's low cellularity and the lack of vascularization, nerves, and lymphatic system. Without treatment, cartilage lesions are known to result in osteoarthritis (OA), the most common joint disease in the world. OA is characterized by fibrillation or wearing of the cartilage surface resulting in articular cartilage degradation, joint pain, and eventually requiring surgical intervention. Total joint replacement (TJR) is currently the only treatment for end stage OA. TJR operations have been projected to continue to escalate based on the aging baby boomer population, increase in average lifespan, and earlier onset of obesity in adults, and increasing activity level of afflicted patients. Current limitations with TJR are its limited lifespan, loss of quality of life (i.e. activity), overall cost (median cost of $28,000/patient), and end point nature. TJR is currently the only treatment for end stage OA with a current U.S. market size of $17 billion. The TJR market size has been projected to grow to $100 billion by 2030. Despite the significant projection in market size increase, regenerative medicine strategies are starting to emerge as a defining treatment to curtail end stage OA and replace damaged cartilage to prevent further cartilage degradation.

Articular Cartilage Regeneration

Some embodiments of the present invention allow for articular cartilage regeneration. Aforementioned, articular cartilage is the cartilage that covers the end of long bones (e.g. tibia, femur, etc.) and acts as a shock absorber and provides a smooth frictionless surface for articulation. Articular cartilage exhibits anisotropic mechanical properties as a result of depth dependent differences in the density and structural arrangement of its extracellular matrix, which consists predominantly of proteoglycan molecules retained within a fibrillar type II collagen meshwork. The fibrillar collagen meshwork provides mechanical reinforcement and is comprised of four zones, namely the superficial, transitional, radial, and calcified cartilage zones. As a function of these zones, collagen fibers vary in their alignment, progressing from parallel in the superficial region, to random in the middle zone and finally orientating perpendicular to the subchondral bone surface in the deep and calcified cartilage zone. This anisotropic fiber orientation contributes to depth-dependent or zonal mechanical properties in terms of ultimate tensile strength and tensile modulus. From a functional and simplified perspective, cartilage can be classified into three main regions, the superficial zone which exhibits a high tensile strength and low coefficient of friction to maintain smooth articulation, a dense extracellular matrix region which contributes to the compressive mechanical properties by providing a high osmotic swelling pressure within the tissue based on the abundance of proteoglycan molecules and the counterbalance with water, and the calcified cartilage interface that adheres cartilage to bone.

Clinical articular cartilage restoration is an evolving field where established and emerging replacement strategies are being performed within the clinical setting to treat chondral lesions as a means to restore articular cartilage. Current cartilage restorative procedures include bone marrow stimulation, fresh osteochondral allografts (donor tissue), osteochondral autografts (patient's tissue), and autologous chondrocyte implantation (ACI). Despite these numerous techniques there stills lies abundant controversy regarding treatment method. In practice, a given method is selected at the discretion of the orthopedic surgeon based on the size of the defect, location, as well as number of previous surgeries. The ACI technique was first reported in 1997 and involves implanting a patient's own chondrocytes at the defect site. In this technique a biopsy of healthy articular cartilage is arthroscopically harvested from a low or non-load bearing location and the cartilage is enzymatically treated to isolate the patient's own chondrocytes. From this initial cell population of a few hundred thousand, the chondrocytes are expanded to more than 10 million. Following expansion, the cells are injected into the cartilage defect beneath a periosteum patch. The periosteum is a fibrous membrane located on the patient's long bones (e.g. tibia) that is harvested by the surgeon, sutured over the defect site adjacent to the surrounding healthy cartilage, and the expanded cells are injected beneath the membrane.

While classical ACI treatment utilizes a periosteum membrane to retain a cell suspension, certain embodiments of the present invention propose the isolation, expansion, and seeding of expanded cells into implantable devices. Such devices are meant to act as a carrier of the chondrocytes and help with attachment, provide temporary mechanical support, and reside in the tissue defect site. Re-operation rates for classical periosteum-based ACI are up to nearly 40% with complications ranging from graft failure, graft delamination, tissue hypertrophy, and tissue adhesion, among others. Approximately 90% of patients with complications experience transplant hypertrophy, lack of integration with surrounding cartilage, inferior cartilage regeneration, and/or graft delamination. Specific advantages for at least some of the devices and methods for ACI treatment disclosed herein over periosteum-based ACI treatments may include, for example, the removal of specific complications including patient morbidity at the harvest site, variability in periosteum physical properties (based on anatomical location, harvest technique, thickness, regenerative capacity), as well as reoperation rates caused by periosteum failure and poor tissue growth. As described herein, device based ACI also features enhanced fixation mechanisms to prevent delamination and support integration of the device into surrounding tissues, in certain embodiments.

One challenge in cartilage restorative therapies lies in generating improved tissue durability and functional improvement. Aforementioned articular cartilage is a highly organized, fiber-reinforced tissue that provides a low-friction and wear-resistant bearing surface comprised of four main zones, the superficial, transitional, radial, and calcified cartilage zones. It is believed that the superficial zone provides a smooth lubricating surface and high tensile mechanics, the transitional and radial zones are comprised of bulk proliferating and compressive zone where the majority of its compressive properties are generated, and the calcified cartilage zone is the cartilage/bone interface which anchors cartilage to bone and allows for force transmission. The mechanical properties of this tissue vary based on the specific zone of cartilage; bulk properties of articular cartilage include a tensile modulus (stiffness) of 5-25.5 MPa and compressive modulus of 0.1-2 MPa, and a smooth articulating surface with surface roughness ($R_a$) 0.1-1 µm and frictional coefficient ($\mu$) of 0-0.5.

In some embodiments of the present invention, one or more factors for selecting and designing the device include, for example, 1) the type of tissue to be generated (articular cartilage possesses zonal organization and unique architecture that is associated with its overall function), 2) the need for sufficient integration with bone, 3) whether a smooth and/or lubricating surface is desired, 4) optionally, a highly porous region for extracellular matrix deposition, 5) the possibility for an open-edge porous structure to allow lateral integration with the native tissue, 6) the need for adhesion to subchondral bone, 7) desired mechanical properties such as tension, compression, shear, and coefficients of friction, and 8) the availability of improved attachment methodology for adhering the device into the tissue (including for example transosseos fixation of one fabric) and suturing of the other fabric to the surrounding healthy cartilage tissue. The fixation of the device in vivo may assist with its placement and performance, and there are a variety of attachment mechanisms available. The additional use of tissue adhesives is also conceived. For example, a fabric fixation point can be adhered to tissue near the placement site employing a suitable tissue adhesive. Suitable tissue adhesives include, but are not limited to, fibrin glue, cyanoacrylate, thrombin, transglutaminases, and gelatin-based adhesives, amongst others. Tension-based fixation can employ fabric fixation points which can act as suture attachments or fixation points that provide tension to the device through a downward (boneward) force attached to or through bone. Shear-based fixation involves fixating a fabric to the surrounding tissue and can include a fabric overlap to act as a plug to enhance the integration between the surrounding healthy cartilage tissue and the device. The fabric overlap can be substantially uniform around the circumference of the device, or in some regions of the fabric, the overlap can vary, with some regions having more and other regions having less of an overlap, or none at all. In some cases, one or more properties of an implantable device made according to the present invention can be guided by reference to the properties exhibited by the natural tissue the device will replace or repair.

Meniscus Tissue Regeneration

Further embodiments of the present invention allow for meniscus tissue regeneration. The menisci are two wedge-shaped semilunar discs of fibrocartilageneous tissue. Menisci are functionally a dynamical tissue where they aid in force distribution, stability, and provide lubrication surfaces between the tibial plateau and femoral condyles. The menisci are attached to the transverse ligaments, the joint capsule, the medial collateral ligament and the meniscofemoral ligament. Based on their functional role, intact menisci occupy 60% of the contact area between the articular cartilage of the femoral condyles and the tibial plateau, and transmit greater than 50% of the axial load applied in the joint. The menisci are able to undergo high degrees of loading based on the arrangement of extracellular matrix components (mainly type I collagen in dense bundles in a circumferential pattern) which prevent radial extrusion of the tissue. Based on the circumferential orientation of the collagen bundles, this tissue exhibits anisotropic tensile properties with a tensile modulus of 100-300 MPa in the circumferential direction and approximately 10-30 MPa in the radial direction. The overall aggregate modulus of the tissue is in the range of 100-200 kPa. Due to its unique wedge-shape, the menisci are well suited for distributing loads from the curved femoral condyles to the flat tibial plateau. Menisci also demonstrate zonal organization varying from an avascular to vascular zones radiating from the inside-out; these transition zones are known as the white-white zone (avascular), red-white zone (interface), and red-red zone (vascular).

The overall pathophysiology of this tissue is significant as it accounts for the most surgical procedures performed by orthopedic surgeons. Meniscal tears are classified based on the location, thickness, and overall stability of the joint and include zonal location (i.e. red-red) as well as the type of tear. For most meniscal tears, partial meniscus removal is common therapy though it is well known that even partial removal will likely result in accelerated degeneration of articular cartilage, resulting in osteoarthritis.

Certain embodiments of the present invention can be designed to exhibit high tensile strength, compression properties (specifically, recovery after loading), an ability to be conformed to a variety of shapes and sizes, and/or any other suitable parameter. Within the knee joint there are two menisci: the lateral (outside of knee joint) and the medial (inside of knee joint). The dimensions for an adult meniscus vary for the lateral (approximately 33-36 mm in length and 26-29 mm in width) and medial (while the dimensions for the medial are 40-46 mm in length and ~27 mm in width), with thicknesses ranging from 3-6 mm. Some embodiments of the present invention can be shaped to fit a variety of shapes while having regional variations in both tensile properties based on the in-plane variation of the courses and wales as well as compression properties. Fixation of the device in vivo may assist with its placement and performance, in some embodiments, and there are a variety of attachment mechanisms available. Fixations are based on tensioning load systems which can involve the drilling of a tunnel through the bone between the attachment point and an opposite surface, and/or suturing to the tibial plateau, and the additional use of tissue adhesives is also conceived. In some applications, it may be beneficial to replace the both the meniscus and the bone it is attached to. In addition to primary fixation, it is understood that in order to assist correct surgical placement the device could require a range of secondary fixation systems and include sutures pre-embedded into the device or guide sutures externally attached to it. Tension based fixation include fabric fixation points which are regions of either the first fabric, the second fabric, or a combination thereof which can act as suture attachments. Shear based fixation is comprised of fixating a fabric to the surrounding tissue and can include a fabric overlap to act as a plug to enhance the integration between the surrounding healthy tissue and the device. The fabric overlap can be substantially uniform around the circumference of the device, or in some regions of the fabric, the overlap can vary, with some regions having more and other regions having less of an overlap, or none at all. These devices can be used not only as a mechanical replacement for meniscus tissue, but also as a carrier for cells for potential regeneration.

SUMMARY OF INVENTION

Some embodiments of the present invention relate to an implantable device for the replacement or repair of musculoskeletal tissue, comprising: a first fabric, a second fabric, a plurality of spacer elements connecting the first fabric to the second fabric, wherein the first fabric and the second fabric define an interfabric space, and optionally a fabric fixation point provided by the first fabric, the second fabric, or both.

To improve the treatment options with device-based musculoskeletal tissue devices, engineered textile fabrics offer a solution. Fabrics are comprised of yarns which can either contain a single filament (also known as a monofilament) or multi-filament yarns containing more than one individual filament. Monofilaments can be identified by diameter of the cross section. Multifilament yarns can be identified by their linear density or denier and filament count. More specifically, denier can be defined as mass in grams for 9000 meters of yarn. Higher denier values relate to heavier, thicker yarn while lower denier values relate to thinner, lighter yarn. For instance, 150 denier yarn has twice the thickness of 75 denier yarn with all other parameters being the same. Yarns typically have rounded or circular cross-sections, but can also be formed with varying cross-section patterns such as tri-lobal, multi-lobal, rectangular, amongst other designs.

Yarns can also be engineered to have a core-shell configuration where the outer area of the yarn also referred to as the shell can have varying properties respective to the inner area or core of the yarn. Fabrics are based on the arrangement of yarns into engineered constructions, of which there are four types: woven, knitted, braided, and nonwoven. Knit structures offer high conformability/drapability, tailored permeability, delamination resistance, fracture toughness, and impact resistance. Knitting is a technique where a two-dimensional mesh or fabric is constructed by the highly ordered arrangement of interlocking loops. The knitting process produces fabrics by interlooping yarns using knitting needles where a continuous series of loops is formed by drawing yarn through the previously formed loop to form a new loop. During the knitting process, yarn is stored on large containers known as beams and is fed from the beams into a knitting machine. The number of yarns on the beams can vary based on the number of knitting elements (i.e. needles) used. Or, in some embodiments, a beam can be partially threaded, for example, when a more porous knit is desired. In certain embodiments, the beam holds the yarn that is fed into a knitting machine. The number of yarns can vary and different beams are used to make the different fabrics. 'Partially threaded' simply means that the beam for one fabric does not have the same number of yarns as the beam that is producing another fabric. Where the fabrics are constructed using the same knitting needles, yarns that are left out create 'holes' or voids in the fabric. In knitted structures, rows running across the width of the fabric are known as courses and columns running along the length of the fabric are known as wales. Knitted fabrics can be identified based on the number of courses or wales per unit length such as course per inch (cpi) or wales per inch (wpi) and correspond to the number of loops per unit length. The number of loops in a measured area is referred to as the stitch density and refers to the total number of loops in a measured area of fabric. Stitch density is calculated by the number of courses and multiplying by the number of wales for that respective area. During the knitting process, the amount of yarn used to construct the fabric can vary based on the amount of yarn fed into the knitting machine. By controlling the amount of input yarn or runner feed length (the amount of yarn run into a knitting machine) the fabric can have varying shrinkage, extensibility, tensile, and friction properties. For instance two fabrics with the same textile pattern but different runner lengths will have different properties based on the amount of yarn incorporated into the same unit area. For example to create a tighter knit structure, shortening the runner feed length will condense the fabric structure, while a fabric with the same knit pattern but with a higher runner feed length will yield a denser fabric and looser knit structure. Additionally the textile pattern can vary based on how the courses and wales are interconnected (stitch notation) depending on the movement of needles, as well as machine type either being weft (also referred to as circular) or warp knitting.

Devices, in some embodiments of the present invention, are a combination of two outer fabrics that are separated and joined together by a layer of interconnecting yarns and/or monofilaments. In general, devices can contain either woven fabrics that are then knitted together or are formed completely by knitting the two outer fabrics and interconnecting with the interconnecting yarns (also referred to as a plurality of spacer elements) in a single continuous process. When regarding the orientation of the device, solely for ease of reference and not for limitation, the x direction and the y direction refer to the plane of the fabrics, and the z direction extends across the interfabric space between the two fabrics. The plurality of spacer elements extend substantially in the z direction. Of course, it will be appreciated that the fabrics and the device are not necessarily "planar" or flat, but can appear in any suitable geometrical arrangement.

Embodiments of the present invention can be made according to any suitable method. For example, knitted devices can be constructed from warp knitted or weft knitted machines. Warp knitted devices can be formed on a rip Raschel machine, while weft knitted devices are formed on a double jersey circular machine with a rotatable needle cylinder and needle dial, in some cases. Varying knitting parameters include yarn size (denier), yarn filament count (number of filaments per yarn), yarn runner feed length, number of needle bars, number of yarn ends, amongst others. The advantages of certain devices, in some embodiments, are that they yield a singular three-dimensional device formed between two separate planar fabrics interconnected by a plurality of spacer elements providing interfabric space between the two fabrics, outstanding integrity between the two fabrics, debonding resistance between the two fabrics, as well as compression properties including compression resistance (i.e. stiffness) and recovery after each loading/unloading cycle. Due to the plurality of spacer elements being knitted into the first fabric and second fabric, in some embodiments, the plurality of spacer elements are held under tension to maintain the interfabric space. In addition to providing the interfabric space, the plurality of spacer elements also provides compression resistance based on the rigidity or stiffness of the monofilament or multifilament yarn of each spacer element. This interfabric space provides a region for loading of biological materials as well as an area that can allow the ingrowth of tissues to integrate the device with surrounding native tissues.

In order for these devices to function, proper integration in vivo may be used in some embodiments. Such integration, in certain cases, relies on a suitable fixation mechanism. As such, fixation of these devices is based on a combination of strategies that utilize the fabric itself to generate a fabric fixation point that incorporates either the first fabric, the second fabric, or both fabrics including adaptive inclusive fixations. The fabric fixation points are used as a fixation mechanism and can include combinations of both tension and shear induced fixation to surrounding tissues. Secondary fixation systems can also be used which include sutures pre-embedded into the device, guide sutures externally attached, tissue adhesives, staples, or any other practiced means.

BRIEF DESCRIPTION OF THE DRAWINGS

FIGS. 1-6 include a diagrammatic side view of articular cartilage and a side view and isometric view of a device featuring the two optionally planar fabrics and the interconnecting yarns forming the plurality of spacer elements.

DETAILED DESCRIPTION

Figure 7:
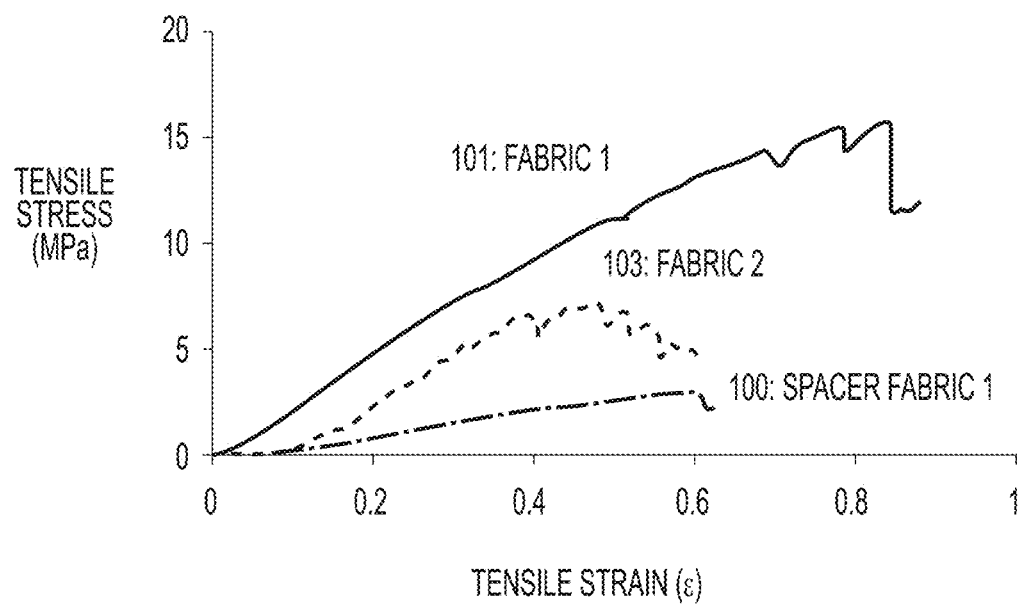
FIGS. 7-11 show an example of tensile testing of a device containing two different fabrics which exhibit different tensile properties based on varying fabric construction for the first fabric and second fabric.
Figure 8:
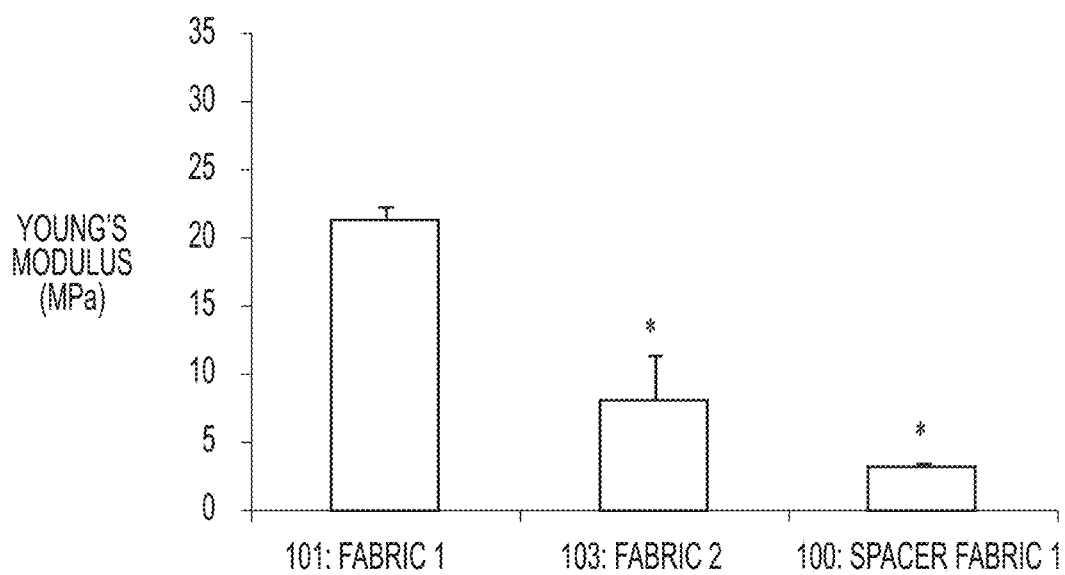
Figure 9:
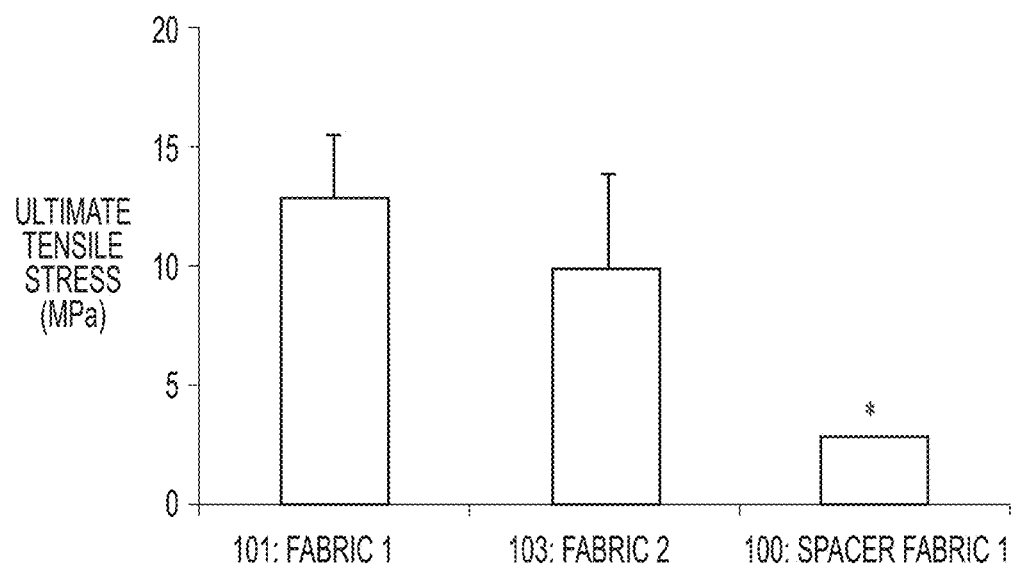
Figures 10, 11:
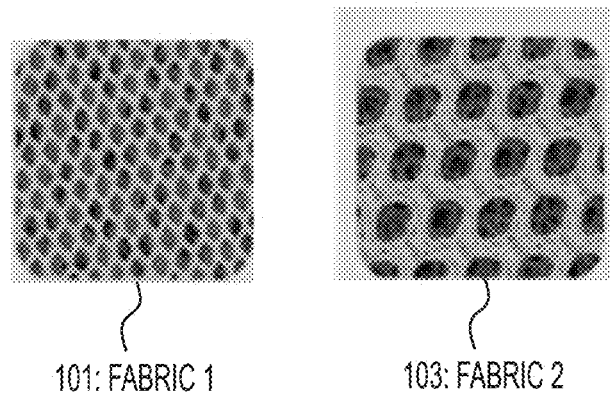
Figure 12:
FIGS. 12-17 show diagrammatic views of a device featuring different designs for articular cartilage replacement based on changing the design of the plurality of spacer elements.
Figure 13:
Figure 14:
Figure 15:
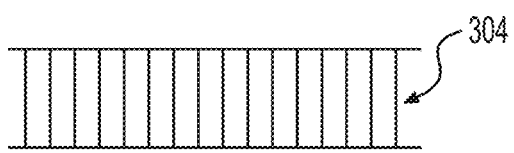
Figure 16:
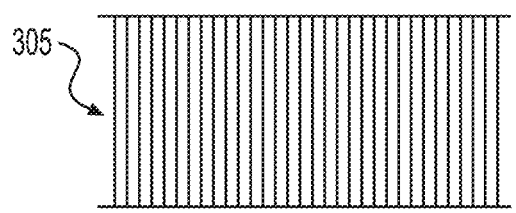
Figure 17:
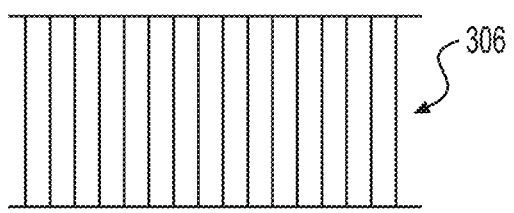

In light of the disadvantages with current implantable devices aimed at musculoskeletal tissues, at least some embodiments of the present invention offer significant advantages due to their flexible design. For example, factors that are relevant for the replacement of articular cartilage include 1) frictional/surface properties for low abrasion resistance on the first fabric, 2) compression property control based on the plurality of spacer element constraints, 3) tailored porosity for tissue ingrowth/adhesion on the second fabric, and 4) proper fixation mechanism into the native tissue. As an illustrative embodiment of the invention as shown in FIGS. 1-6, a device (100) can be designed by reference to the structure and organization of articular cartilage (130). The device (100) includes a first fabric (101), a second fabric (103), and a plurality of spacer elements (102) connecting the two fabrics. In this embodiment, each of these components can be engineered to match the mechanical/functional properties of articular cartilage as well as the size of defect in regards to area and depth (i.e. thickness of the device created by the plurality of spacer elements (102)). In certain embodiments, the design of the fabrics (101 and 103) will determine the orientation and placement position of the device into the defected joint area. First fabric (101) will be in direct contact with the joint capsule undergoing articulation or sliding motion in the joint, while the second fabric (103) will be in direct contact with the underlying bone following removal of the damaged cartilage tissue. This orientation will place the plurality of spacer elements (102) in direct contact with the adjacent healthy cartilage allowing integration between device (100) and the native healthy tissue.

Based on its orientation in the joint, the first fabric (101) can be designed to provide an articulating surface by having smooth surface features and exhibiting high tensile strength. Abrasion resistance for knitted fabrics is based on the yarn and fabric construction parameters. The abrasion resistance of a yarn is influenced by several factors: the denier of the yarn, the number of filaments within the yarn (higher number of filaments results in a softer, smoother surface), the amount of twist in the yarn that binds the filaments together (the lower the twist, the lower the resistance), the orientation of molecules in the filaments (the higher the orientation, usually the lower the resistance), and the surface coefficient of friction. Note the lower the denier, the smaller and finer the yarn; while higher denier refers to heavier and coarser yarn. Therefore lower denier, high filament count yarns, high-twist yarns, smooth surfaces, and highly-oriented molecules generally exhibit higher abrasion resistance. In certain embodiments the denier for the yarn in the first fabric can range from 20-70 denier. In other embodiments the filament count for multi-filament yarns can vary from 18-96, with filament counts ranging from 36-96 filament count being suitable for the articulating surface and for the first fabric. Knitting parameters can also be optimized to generate a high stitch density to generate a tighter structure. For instance, the amount of yarn fed into the knitting machine can be decreased to increase the loop density, which would increase the tensile properties, and lower the surface roughness. For example, a tighter knit structure can result in higher yarn-to-yarn contact and proximity, resulting in smaller pores, smoother surface, and higher tensile properties. In certain embodiments, the first fabric can be constructed from more than one yarn type which may be selected based on yarn characteristics such as denier, material, chemistry, amongst other criteria.

The second fabric (103) can be designed to allow tissue ingrowth from the underlying bone by having enhanced porosity, roughened surface, and the incorporation of biologically active material into the yarn. Biologically active materials are materials that can elicit a biological response when implanted into a patient. Suitable biologically active materials include, but are not limited to, enzymes, peptides, proteins, cells, tissues, drugs, growth factors, ions, inorganic components and bioactive glasses, and combinations thereof. In some embodiments the second fabric can be constructed of different yarns from that of the first fabric. To facilitate tissue ingrowth into the device (100), one or more parameters can be modified to create the optimal settings. Such factors include, but are not limited to, the use of yarns that include any suitable inorganic or mineralizing component to promote mineralization to the adjacent bone surface and the design of the second fabric (103) to promote tissue ingrowth. Employing yarns of larger denier from 20-160 denier can also facilitate tissue ingrowth. In some embodiments the filament count in the yarn can vary from 18-44 filaments per yarn. To create a looser knit structure, lengthening the yarn runner feed length will generate a looser textile pattern. Tissue ingrowth can be optimized by creating voids in the second fabric (103), such as by removing yarns in the fabric structure to create an open hole or mesh network, generating large voids. A mesh network can be formed by knitting in a pattern known as an open hole network or mesh and is widely known to those skilled in the art. For example, this is known as partially threaded beam, where one beam that is used to construct the second fabric has yarns removed so that there are fewer input yarns creating the second fabric. In some embodiments, up to 80% of the surface of the second fabric (103) can be voids allowing tissue ingrowth (103). To promote mineralization and adherence with the adjacent underlying bone surface, composite yarns containing chemical components capable of releasing soluble by-products such as enzymes, peptides, proteins, and/or ions can be incorporated into the device (100), and the second fabric (103) can be wholly or partly comprised of such yarns, for example. Suitable ions include ions of calcium, magnesium, strontium, silicon, cobalt, phosphate, and enzymes such as alkaline phosphatase, amongst others. These components can be incorporated into the yarn during formation process such as melt-spinning to form composite yarns. In some embodiments the second fabric (103) can be loaded with up to 1-30 wt % inorganic particles. In some embodiments the yarn can be preferentially loaded with inorganic particles in the outer shell of the filament of the yarn known to those skilled in the art as core-shell filament where the shell is the outer portion of the filament and the core is the inner portion of the filament of the yarn. In some embodiments, mineral formation can be achieved on yarns by soaking in a mineral rich solution known as simulated body fluid (SBF). SBF can have the ionic composition of body fluid at several magnitudes higher and be used to induce mineral formation. Enzymes can also be provided by soaking the yarn in an enzyme rich solution and adsorption of the enzyme on the surface of the yarn. In other embodiments both the first fabric (101) and second fabric (103) can be formed from composite yarns for regeneration/replacement of calcified tissues such as bone. In some embodiments, the second fabric can have fabric fixation points (105) which can be used as anchoring points of the device (100). The fabric fixation points are extensions of the second fabric where the plurality of spacer elements have been removed (thus disconnecting this portion of the second fabric from the first fabric) creating a fabric fixation point that resembles a tab or tether. These fabric fixation points (105) of the second fabric allow the attachment of sutures (106) to secure the device (100) in the defect site and can range from 1 to a multitude of fabric fixation points based on the size and severity of the defect. The number of fabric fixation points can vary and in some embodiments includes at least four fabric fixation points. The fabric fixation points (105) can be reinforced with sutures, yarn, amongst other means to enhance their tensile properties. Additional anchorage and attachment in the defect site can be provided by a fabric fixation point referred to as a fabric overlap (104) of the first fabric (101) where the plurality of spacer elements are removed and the first fabric features a fabric overlap (104) adjacent to the surrounding tissue allowing it to be sutured in-plane via a suture amongst other attachment mechanisms (107). The fabric overlap can be substantially uniform around the circumference of the device, or in some regions of the device, the overlap can vary, with some regions having more and other regions having less of an overlap. In some embodiments the fabric overlap (104) can feature a finished edge.

In some embodiments, the variation in fabric construction of the two fabrics (101, 103) can result in varying tensile properties. Tensile mechanics can be engineered to be within the physiological range for articular cartilage based on the functional roles of its different zones (i.e. high tensile modulus for articulating surface and lower tensile modulus for bone interface). As illustrated in FIGS. 7-11, the tensile mechanics for the fabrics (101 and 103) vary significantly when tested individually. For this test, device (100) was constructed on a rip raschcel warp knitting machine with two varying fabrics (101 and 103) by varying the loop formation to form the first fabric (101) with a knit construction and textile pattern and a second fabric (103) with an open hole structure forming a mesh. Yarn was comprised of polyethylene terephthalate with a denier of 70. Individual fabrics (101 and 103) were separated from the device and tested singularly. FIG. 7 illustrates the stress-strain behavior of the faces of the fabrics (101 and 103), and the intact device (100). Tensile testing further revealed that the stiffness or tensile modulus (FIG. 8) varied significantly as did ultimate tensile strength (FIGS. 9-11) for both fabrics (101 and 103). When tested as an intact device (100), the tensile properties are significantly lower based on the increased thickness (area) of the device due to the addition of the plurality of spacer elements between the first and second fabric; (n=3; *=p-value<0.05). This embodiment demonstrates that though device (100) is a singular device, it displays zonal variations in tensile mechanics for the fabrics (101, 103) which match articular cartilage behavior and function.

The plurality of spacer elements (102) is a plurality of yarns that connects the two fabrics allowing for device recovery following loading/deformation and also to withstand compressive forces experienced in the joint. Compressibility can be defined as a decrease of initial fabric thickness due to appropriate increase of compressive force. For the knitted device, the plurality of spacer elements can be a monofilament transversing and interlocking with courses present in both fabrics. The plurality of spacer elements are able to impart one or more of the three-dimensional nature (thickness in the z-direction), elastic recovery, compressive mechanics, and open structure in certain embodiments of the present invention. Characteristic attributes for the plurality of spacer elements may include, for example, polymer type, multi-filament or monofilament yarn, yarn/monofilament size (denier/diameter), distance between the knit fabric surfaces, and density of the plurality of spacer elements. Monofilament yarns may be much stiffer than multifilament yarns and with all other factors constant, the bending stiffness of a monofilament of denier T will be roughly n times greater than a multifilament structure with n filaments of denier T/n each. In other embodiments for the device the distance between the two fabrics can be varied while maintaining the same compression properties (FIGS. 12-17). Based on geometrical relationship between the plurality of spacer elements and fabric thickness, compression properties can be tailored based on the height of the plurality of spacer elements (compare, for example, devices (301) versus (303) versus (305)), and the number of said spacer elements within the plurality of spacer elements per unit area (compare, for example, devices (301) versus (302), (303) versus (304), and (305) versus (306)). To calculate the maximum force the plurality of spacer elements can withstand, F, we can use Equation 1 where E is the modulus of a single spacer element within the plurality of spacer elements, I is the moment of inertia of a single spacer element within the plurality of spacer elements, h is the height of the plurality of spacer elements or the distance between the fabrics, and μ is a known coefficient.

$$F = \frac{\pi^2 EI}{\mu h^2} \quad \text{Equation 1}$$

The modulus of one spacer element within the plurality of spacer elements is based on the polymer type, where the moment of Inertia I is the ability of a material to resist bending where:

$$I = \frac{\rho h^3}{12} \quad \text{Equation 2}$$

Following that ρ=linear density of one spacer element within the plurality of spacer elements, h=the height of the plurality of spacer elements between fabrics, assuming that the plurality of spacer elements are infinitely thin rigid elements.

$$F = \frac{\pi^2 E\rho h}{12\mu} \quad \text{Equation 3}$$

From the maximum force, we are able to derive the maximum stress ($\sigma_{max}$) based on the number of spacer elements within the plurality of spacer elements (N) per unit area (A).

$$\sigma_{max} = \frac{N\pi^2 E\rho h}{12 A\mu} \quad \text{Equation 4}$$

From equation 4 it becomes relevant that the number of spacer elements within the plurality of spacer elements is directly proportional to the maximum compressive mechanics achievable. Thus devices of varying thickness can be designed to be imparted with the same compression properties in regards to resistance (stiffness) and recovery after deformation or loading (FIGS. 12-17).

Figure 18:
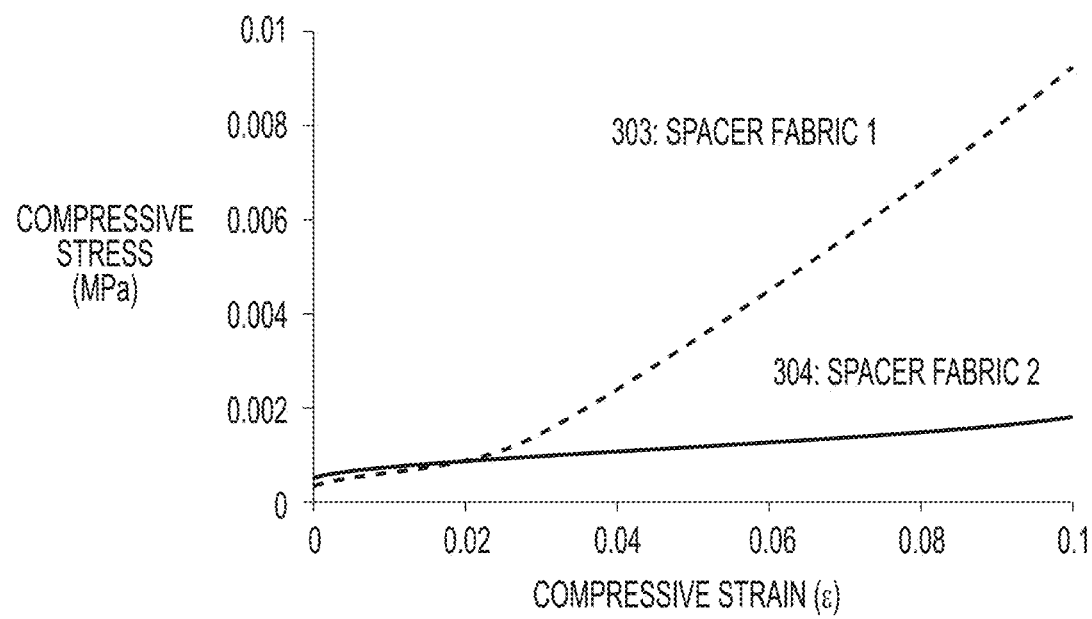
FIGS. 18-21 show an example of compressive testing of devices with different pluralities of spacer elements (density) and resulting compressive properties.
Figure 19:
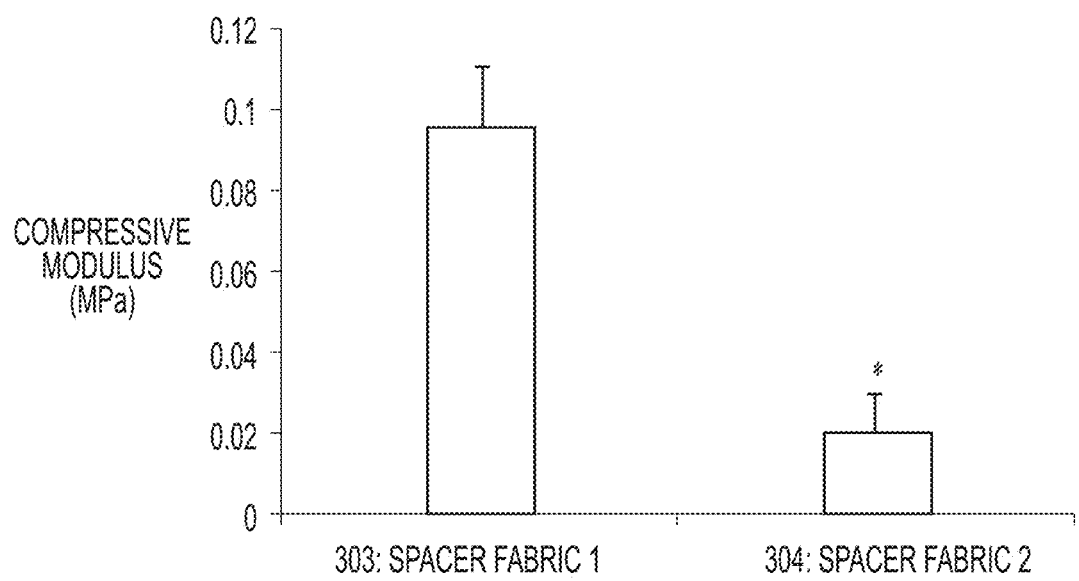
Figure 20:
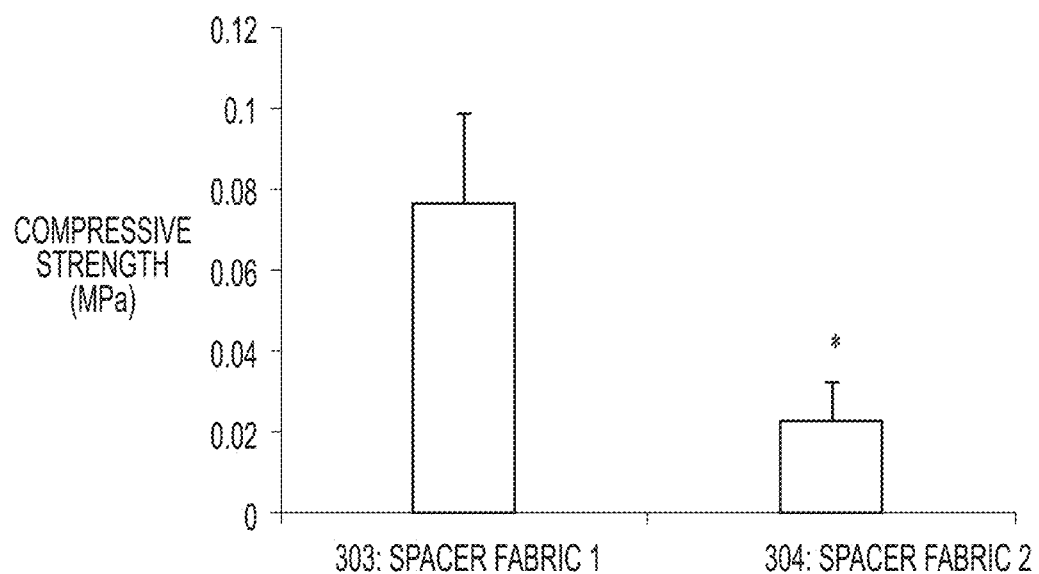
Figure 21:
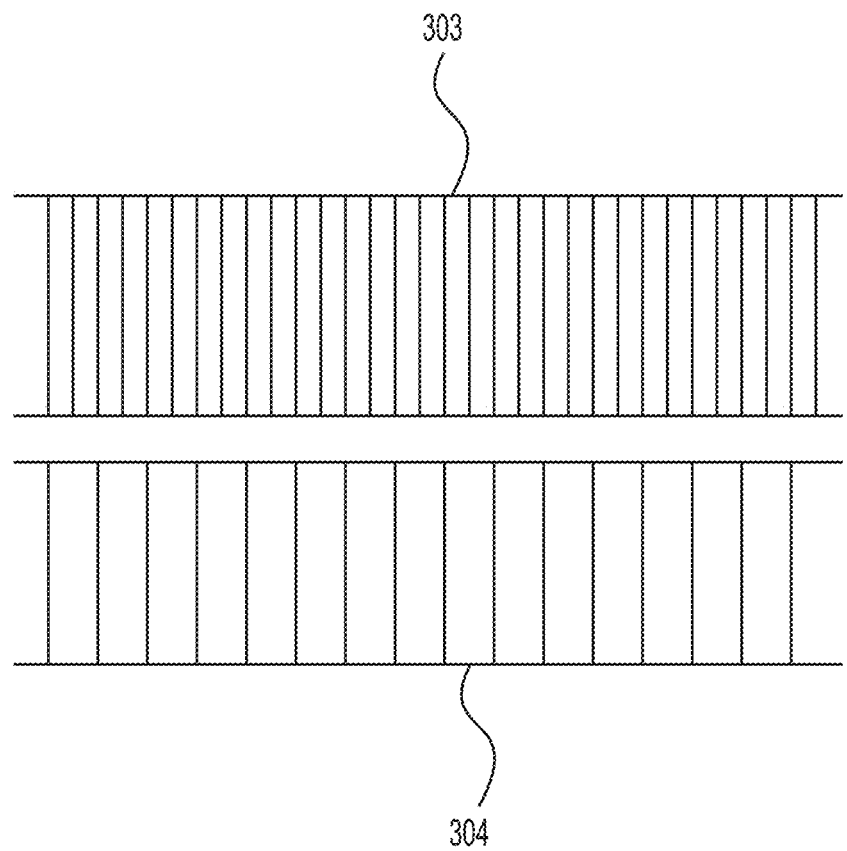

Devices can have varying designs for the plurality of spacer elements including the density (number of spacer elements/unit area), distance between fabrics, and varying alignment of the plurality of spacer elements in regards to the intersection angle or angles between the plurality of spacer elements and the fabric. Embodiments of this variety can encompass tissues of varying thickness while taking into account their compressive properties allowing their functional performance as a shock absorber and resisting deformation from everyday physical activity (e.g., walking). By varying such constraints, the compressive properties such as recovery can vary significantly and be tailored for a range of biological tissues. One illustrative embodiment, FIGS. 18-21, displays the compressive properties of two devices with varying densities of spacer elements in devices (303) and (304). Compressive properties of the devices were measured by applying a force to compress the samples at 0.05% strain/sec in unconfined compression meaning that the samples were not confined on the edge around the device. Compressive stiffness is reported as the linear region of the slope of the stress-strain curve from 0-10% strain correlating to Hooke's law where compressive stiffness E=Δσ/Δε. Compressive strength is reported as the maximum stress achieved up to 10% strain where $\sigma_{max}$=Eε. Devices were constructed on a rip raschcel warp knitting machine and the number of spacer elements within the plurality of spacer elements was varied for device (303) and device (304) from 600 to 300 spacer elements per square cm of fabric. Yarn was comprised of polyethylene terephthalate and the spacer element was a monofilament yarn with diameter of 0.1 mm. The compressive stress-strain behavior (FIG. 18) of each device presented shows two distinct material properties. From the stress-strain curve the compressive modulus or stiffness (FIG. 19) can by calculated which indicates significant difference in the compressive stiffness of the devices (303) and (304) as calculated from 0-10% strain (n=3; * indicates p-value<0.05). As expected the compressive stress also significantly varies (FIGS. 20-21) based on the relationship of the number of spacer elements within the device. This embodiment illustrates a range of compressive properties that can be obtained and demonstrates the tailorability of this device in regards to compression properties.

The plurality of spacer elements (102) creates an interfabric space between the two fabrics (101, 103). This interfabric space provides an area that allows for the loading of biologically active materials including peptides, proteins, cells, tissues, drugs, growth factors, amongst others, and combinations thereof. In some embodiments of the invention, biologically active materials can be placed into the interfabric space by syringe injection, placement with forceps, gravity fed, or any other means to encompass the materials within the interfabric space. Biologically active materials can be of xenogenic, allogenic, or autogenic origin and would promote the growth of new tissue within the device. The interfabric space provided by the plurality of spacer elements (102) provides considerable porosity by the spacer elements consisting of a plurality of yarns preferentially oriented in the z-axis respective of the two fabrics. These yarns forming the plurality of spacer elements are not connected to each other and are merely knit at a point to the first and the second fabric, in some embodiments. Thus the spacer element (102) connects the two fabrics (101 and 103) together by being knitted to each fabric, while also providing compression resistance based on the mechanical property of the plurality of spacer elements to resist force normal along the axis of the plurality of spacer elements. This orientation provides a space that can have a varying porosity of 50-95%. The plurality of spacer elements (102) can be constructed from any fiber-forming polymer. Monofilament diameter in certain cases can range from 0.08-5 mm and in some embodiments the diameter of monofilament diameter is 0.1-0.5 mm. By having a high porosity, the interfabric space can support newly developed tissue growing out from the device to become integrated with the surrounding native tissue (i.e. tissue outgrowth). In some embodiments, this native tissue surrounding the device can grow into the interfabric space also integrating the patient's tissue with the device. In some embodiments, the plurality of spacer elements is knitted into the first fabric and second fabric which puts the plurality of spacer elements under tension to support the fabrics while offering compression resistance based on their rigidity or stiffness.

Figure 23:
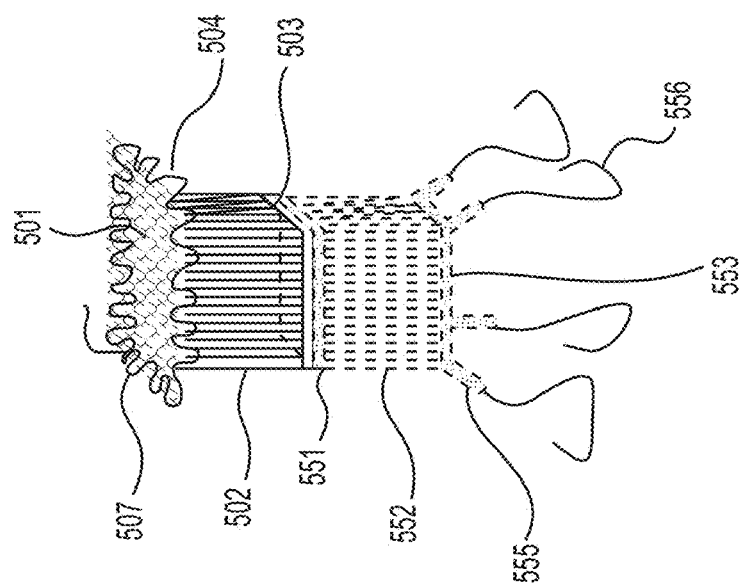
FIGS. 22-23 show diagrammatic views of two adjoined devices forming a dual-layer device for the replacement of interface tissues such as cartilage and bone also referred to as the osteochondral interface or osteochondral junction.
Figure 22:
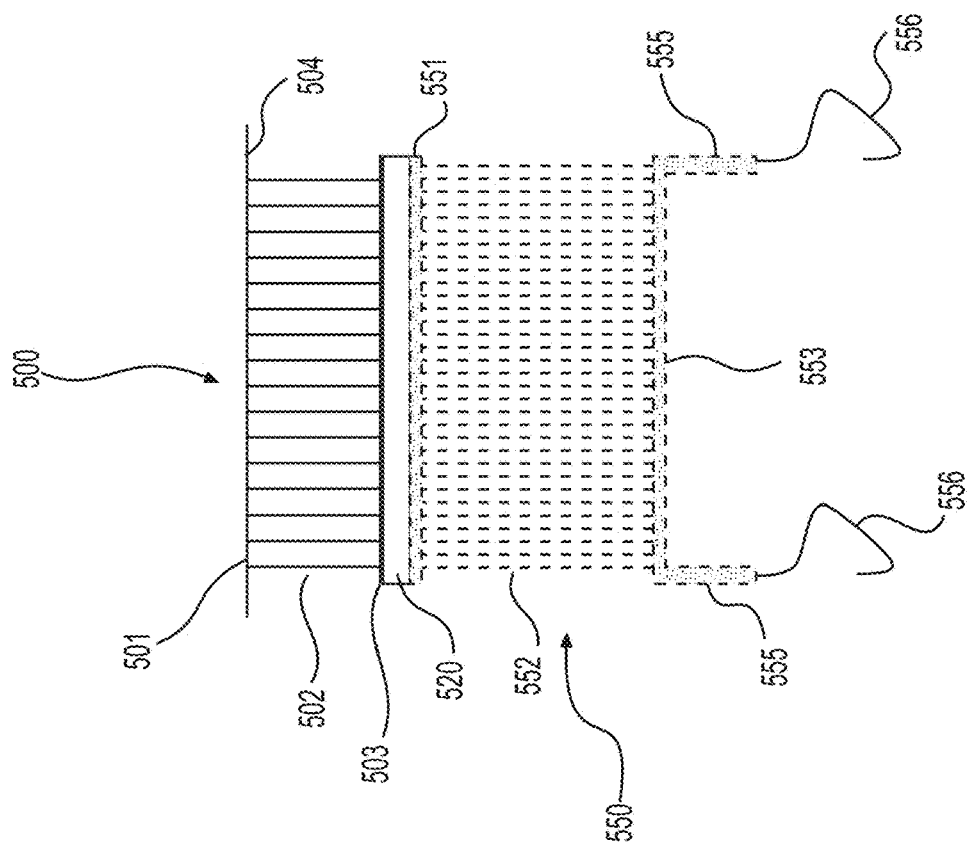
Figure 28:
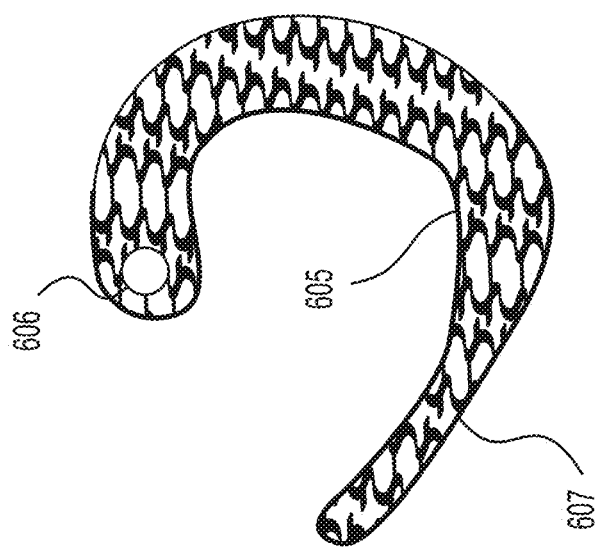
FIGS. 24-28 show diagrammatic side and isometric views of device designed for the replacement of meniscus tissue with and without fabric fixation mechanisms.
Figure 25:
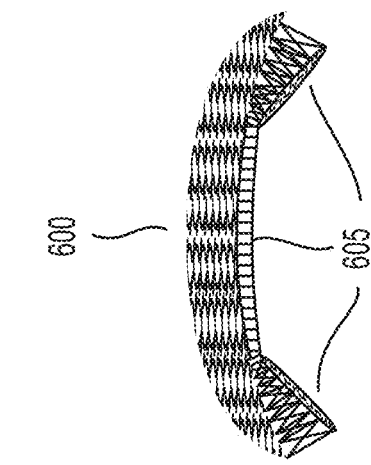
Figure 27:
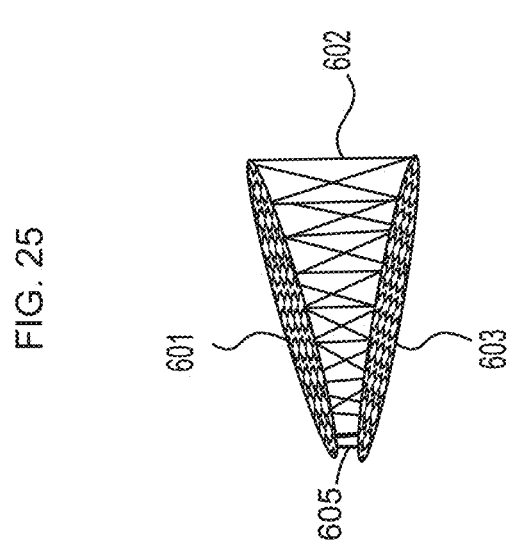
Figure 24:
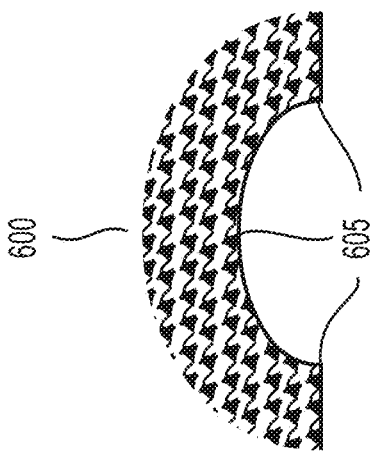
Figure 26:
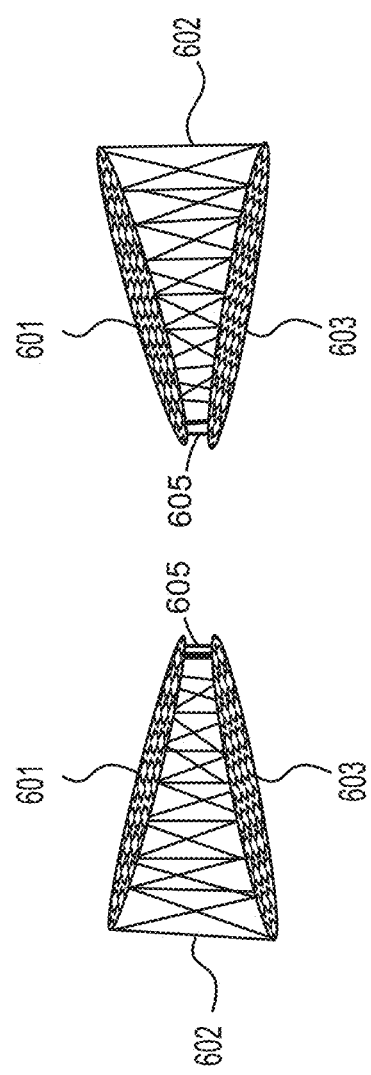
Figure 29:
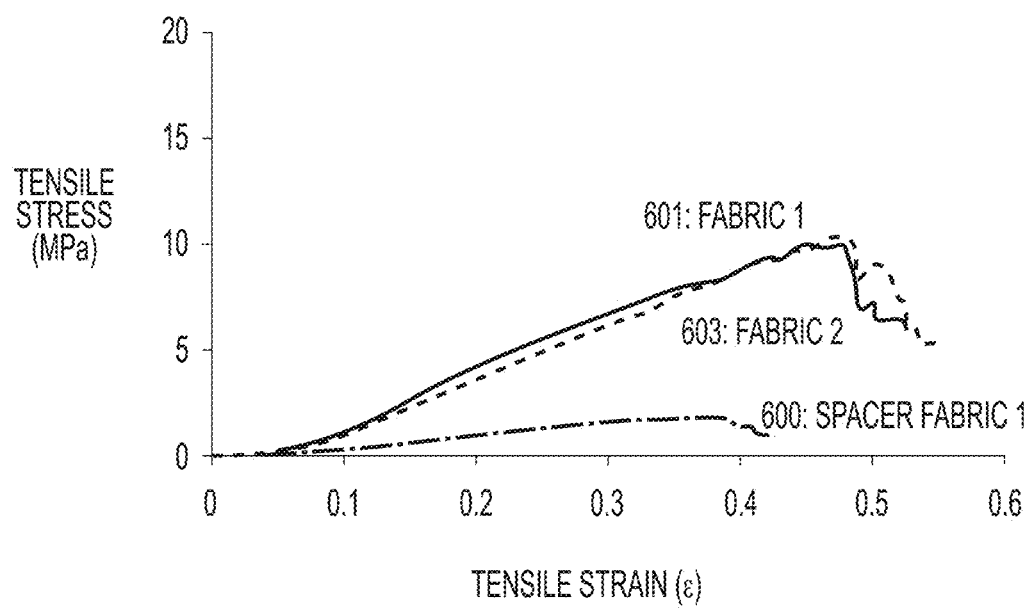
FIGS. 29-33 show an example of tensile testing of a device containing two nearly identical fabrics which exhibit nearly identical tensile properties based on the same fabric construction.
Figure 30:
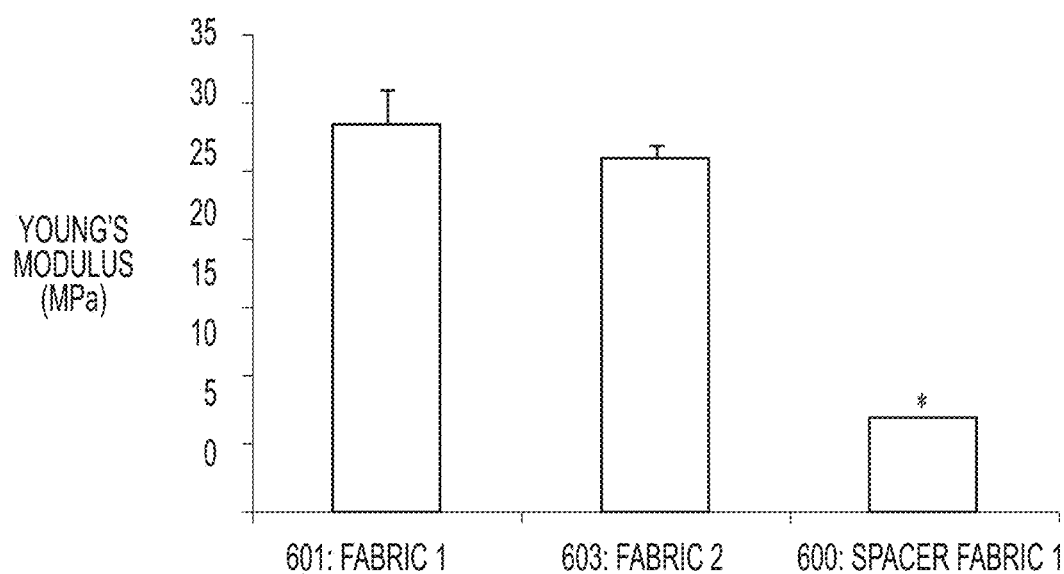

In some embodiments of the present invention, it may be applicable to use more than one singular device by direct combination with another device (FIGS. 22-23). As illustrated in FIGS. 22-23, a dual interfabric space device can be constructed from different devices (500, 550) each having different properties, including tensile, compressive, porosity, amongst others. The device contains a first device (500) having a first fabric (501), a second fabric (503) and a first plurality of spacer elements (502) and a second device (550) having a third fabric (551), a fourth fabric (553), and a second plurality of spacer elements (552). Devices (500 and 550) can be adjoined at the interface (520) by techniques such as suturing, laminating, thermal bonding, or any other means to adjoin two individual devices. This combined device would be desirable in the instance of tissue interfaces such as articular cartilage and bone (i.e. osteochondral) or soft-tissue interfaces (i.e. meniscus-articular cartilage; articular cartilage-ligament/tendon). Based on the joining of multiple devices (500, 550), this can include devices with different properties (i.e. stiffer compression properties for bone and more-yielding compression properties for cartilage, for example), varying degradation rates of the device layers, varying chemistries for suitable tissue regeneration, amongst other combinations. Additionally, the separate interfabric spaces (502 and 552) provide different compartments to load the appropriate biological materials to promote localized tissue growth in the respective areas of the different tissues.

The combined device also can have fabric fixation points (555) located on the fourth fabric (553) which are sections of the fourth fabric that have undergone removal of the second plurality of spacer elements (552). Thus, these fabric fixation points are formed from the fourth fabric (553) but are separated from the plurality of spacer elements (552) and possess enhanced conformability (drape) in order to be fitted into drilled bone tunnels. The addition of these fabric fixation points (555) provide an enhanced attachment mechanism where they can be pulled through pre-drilled bone tunnels to assist with device anchorage. The fabric fixation points (555) can have sutures attached (556) to apply tension to the device (550). The fabric fixation points (555) can be reinforced with sutures, yarn, amongst other means to enhance their tensile properties. Additional embodiments allow for the first fabric (501) to have a fabric fixation point referred to as a fabric overlap (504) that allows the combined device to sit as a plug in a defect. This fabric overlap (504) can be attached to the surrounding tissue using a suture (507) to assist with integration. The fabric overlap can be substantially uniform around the circumference of the device, or in some regions of the device, the overlap can vary, with some regions having more and other regions having less of an overlap, or none at all. In some embodiments the fabric overlap can feature a finished edge. In some embodiments the first fabric (501) can also feature tension-based fabric fixation points to assist with device fixation.

Other embodiments provide a dual-layer device, that is, a device with two interfabric spaces, wherein there is only a single fabric separating the two interfabric spaces. Thus, a first fabric and a second fabric are separated across a first interfabric space by a first plurality of spacer elements, and the second fabric is also separated from a third fabric across a second interfabric space by a second plurality of spacer elements. Such a device can be made in any suitable manner. For example, the first fabric, second fabric, and first plurality of spacer elements can be fashioned together as disclosed herein. Then the second plurality of spacer elements can be woven or knitted into the second fabric, at the same time or sequentially with integration with the third fabric.

As outlined above, at least some devices of the present invention create a porous space between two fabrics. In addition to filling defects of articular cartilage, such devices may also be advantageous for other musculoskeletal tissues such as the meniscus. As previously described, the menisci are two wedge-shaped semilunar discs of fibrocartilagenous tissue. In certain embodiments of the present invention, wedge-shaped devices can be constructed to fit a variety of shapes. Thus, in some embodiments of the present invention, the fabrics of the device do not have to be exactly equidistant nor do they need to be planar but can have varying distance between the fabrics. As illustrated in FIGS. 24-28, devices can be designed to form a variety of shapes for tissue replacement, including the c-shaped meniscus device (600). As illustrated, in device (600), an edge forming yarn (605) can be used to constrain one edge of the device generating a difference in the distance spanned by the plurality of spacer elements (602) between the first fabric (601) and the second fabric (603). The edge forming yarn (605) places the device under additional tension, constraining one lateral edge and minimizing the interfabric space on one edge of the device (600). Additionally, individual spacer elements from the plurality of spacer elements (602) can be removed after device construction (e.g. by cutting) to generate regional variations in compressive properties based on the in-plane variation of the density within the plurality of spacer elements. In some embodiments of the device, both fabrics (601 and 603) of the device (600) may be designed to have the same physical properties such as tensile mechanics, porosity, coefficients of friction, amongst others. Thus, in some embodiments of the device, both fabrics can be comprised of yarn with the same properties and the fabrics can be constructed of the same textile pattern, stitch density, amongst other fabric criteria when it is desired for both fabrics to have similar properties. Additionally, the device (600) can be designed to have fabric fixation points (606 and 607) as illustrated in FIGS. 24-28. These fabric fixation points (606 and 607) are based on the device (600) having a suitable hole for attachment of a screw through a shorter anterior fabric fixation point (606) and a longer posterior fabric fixation point (607) that allows tensioning of the device in situ. The anterior fabric fixation point (606) is comprised of a hole in the device (600) through the first and second fabric to allow placement of an attachment such as a screw to attach the device (600) to bone such as the tibial plateau. The posterior fabric fixation point (607) is comprised of the both the first and second fabric (601 and 603) but features the removal of the plurality of spacer elements (602) by any suitable means such as by cutting. The first and the second fabrics (601 and 603) of the device (600) can then be adhered to one another using stitches, sutures, adhesives, to form a strap-like portion, the posterior fabric fixation point (607), with a cross-sectional area substantially smaller than that of the remainder of the device (600). Additional embodiments allow for the use of secondary suture mechanisms (not shown) around the periphery of the device (600).

Figure 31:
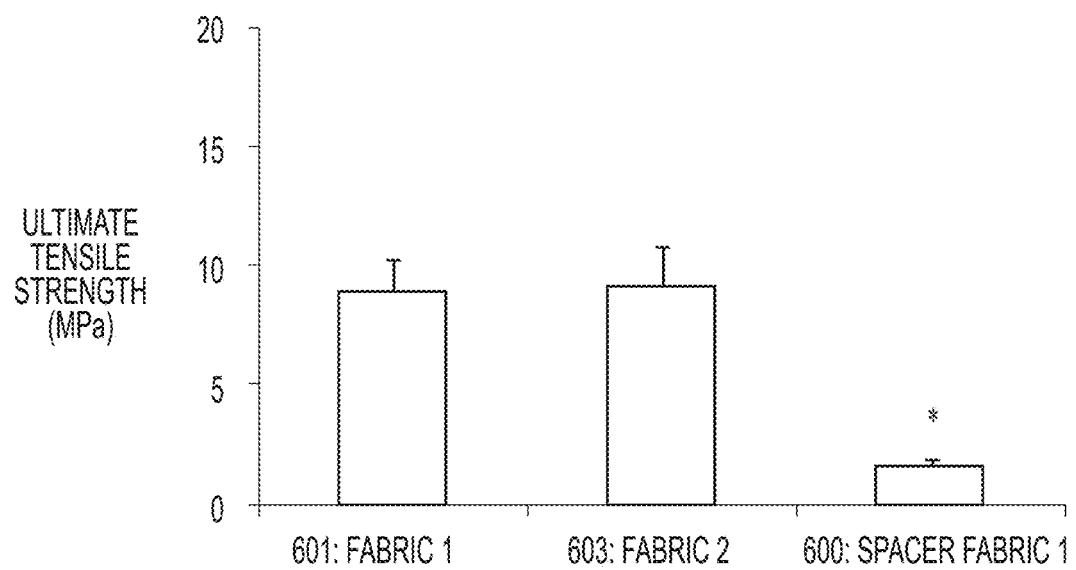
Figure 32:
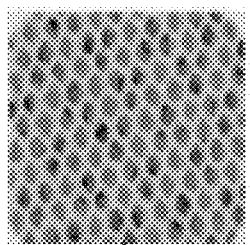
Figure 33:
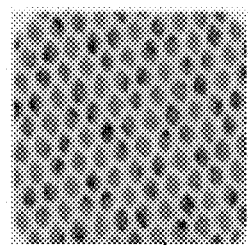

In some embodiments, the tensile mechanics can be engineered to be within the physiological range for meniscus to mimic the functional roles of its surfaces (e.g., high tensile modulus for articulating surface). As illustrated in FIGS. 29-33, the tensile mechanics for the fabrics (601 and 603) are nearly identical. For this test, device (600) was constructed on a rip raschcel warp knitting machine with two identical fabrics (601 and 603) by maintaining the same knit structure for both fabrics. Yarn was comprised of polyethylene terephthalate with a denier of 70. Individual fabrics were separated from the device and tested singularly. As shown in FIGS. 29-33, fabrics (601 and 603) demonstrate near identical stress-strain behavior (FIG. 29), as well as tensile modulus (FIG. 30), and tensile strength (FIGS. 31-33). When tested as a device (600) the tensile properties are significantly lower based on the increased thickness (area) of the device due to the addition of the spacer element; (n=3; *=p-value<0.05). This device design would be ideal for an interface tissue that requires nearly identical properties for both fabrics such as the meniscus.

Figure 35:
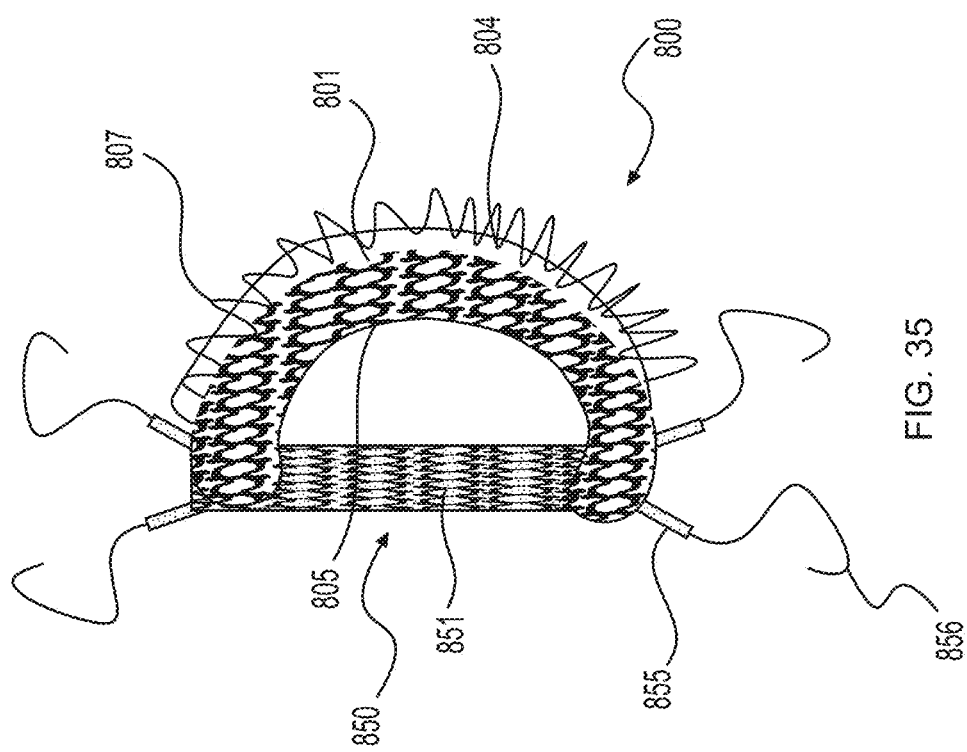
FIGS. 34-35 show diagrammatic views of two adjoined devices forming a dual-layer device for the replacement of interface tissues such as meniscus tissue and bone.
Figure 34:
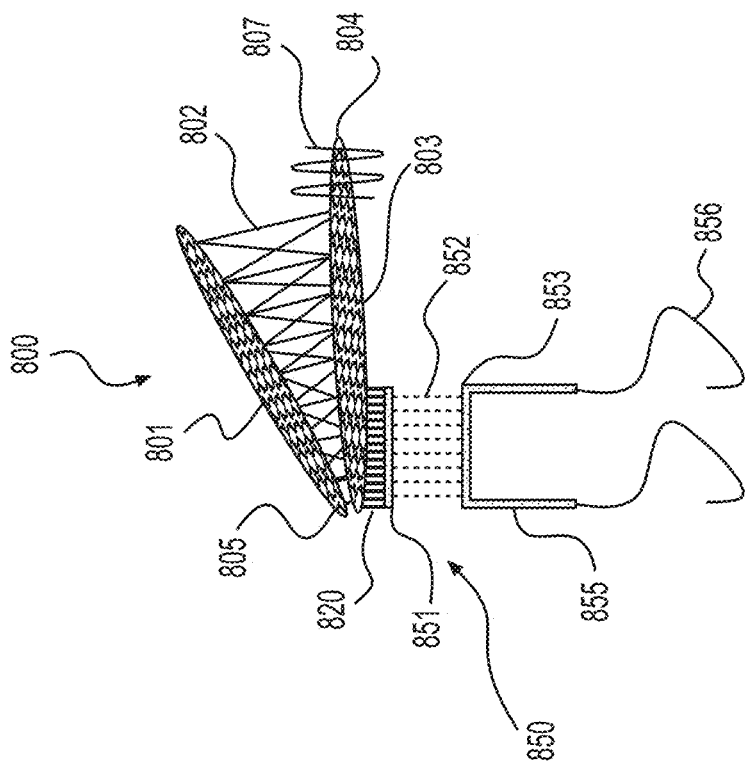
Figure 38:
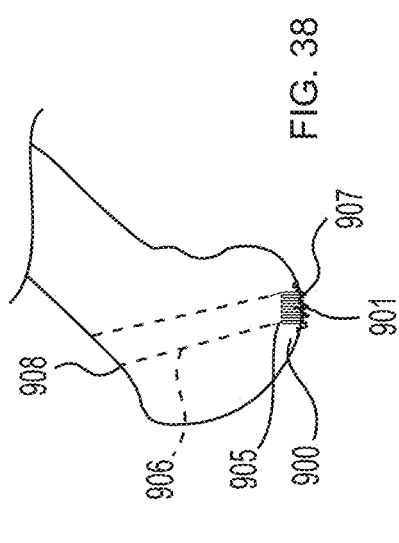
FIGS. 36-41 show an example of implantation strategy for the devices for articular cartilage and osteochondral defects within femoral condyles utilizing a single-layer and a dual-layer device, respectively.
Figure 41:
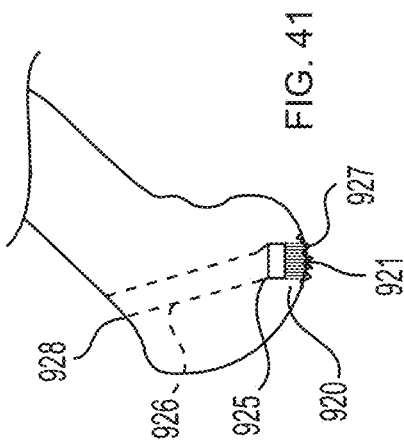
Figure 37:
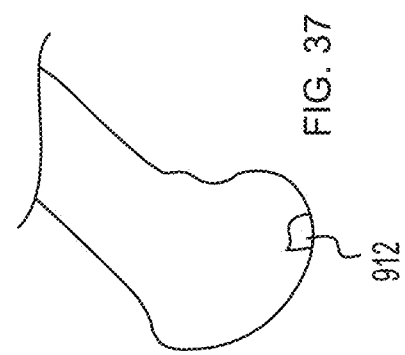
Figure 40:
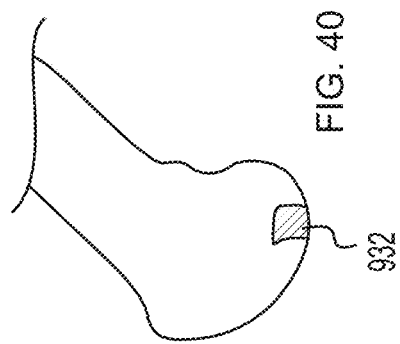
Figure 36:
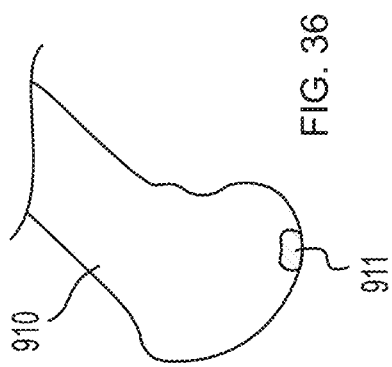
Figure 39:
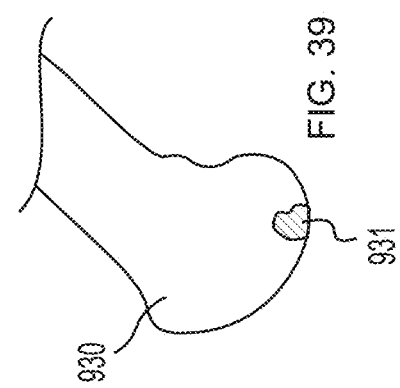

In some embodiments of the present invention, it may be applicable to use more than one singular device by direct combination with another device (FIGS. 34-35) as this can assist with better integration into the defect site and/or used for complex repair procedures (i.e. lateral meniscus). As illustrated in FIGS. 34-35, a dual-layer device can be constructed from different single-layer devices (800, 850) with different shapes, sizes, properties, including tensile, compressive, porosity, amongst others. The combined device is comprised of a first device (800) containing a first fabric (801), a second fabric (803) and a first plurality of spacer elements (802) and a second device containing a third fabric (851), a fourth fabric (853), and a second plurality of spacer elements (852). Single-layer devices (800 and 850) can be adjoined at the interface (820) by any suitable technique such as suturing, laminating, thermal bonding, adhesives, or any other means to adjoin two individual devices. This combined device would be desirable in the instance of tissue interfaces such as meniscus-bone attachment on the tibial plateau of the knee. Based on the joining of multiple devices (800, 850), this can include devices with different properties (i.e. stiffer compression properties for bone and lower compression properties for fibrocartilage (meniscus tissue, for example), varying degradation rates of the device layers, varying chemistries for suitable tissue regeneration, amongst other combinations. Additionally, the separate interfabric spaces (802 and 852) provide different compartments to load the appropriate biological materials to promote localized tissue growth in the respective areas of the different tissues. The combined device can also have fabric fixation points (855) located on the fourth fabric (853) which are sections of the fourth fabric (853) that have undergone removal of the second plurality of spacer elements (852) and are not attached to the third fabric (851). Thus, these fabric fixation points (855) are formed from the fourth fabric (853) but are separated from the second plurality of spacer elements (852) and possess enhanced drape in order to be fitted into drilled bone tunnels. The addition of these fabric fixation points (855) provide an enhanced attachment mechanism where they can be situated through pre-drilled bone tunnels to assist with device anchorage. The fabric fixation points can have sutures (856) attached to apply tension to the combined device. The fabric fixation points (855) can be reinforced with sutures, yarn, amongst other means to enhance their tensile properties. Additional embodiments allow for the first device (800) to have a fabric overlap (804) provided by the second fabric (803) that allows the device to be attached to edge of native tissue. This fabric overlap (804) can be attached using a suture (807) to assist with integration with the surrounding tissue. The fabric overlap (804) is merely an extension of the second fabric (803) that has been separated from the first plurality of spacer elements (802), and is not connected to the first fabric (801). Additionally, the fabric overlap (804) is around the edge of the first device (800) and provides a secondary, local attachment mechanism to support proper device placement. Tension based fixation include fabric fixation points which can act as suture attachments. Shear based fixation is comprised of fixating a fabric to the surrounding tissue and can include a fabric overlap to act as a plug to enhance the integration between the surrounding healthy cartilage tissue and the device. The fabric overlap can be substantially uniform around the circumference of the device, or in some regions of the device, the overlap can vary, with some regions having more and other regions having less of an overlap. In some embodiments of the invention replacement of such tissues requires the implantation of a device (e.g., 100, 500, or 600) that is implanted into the target site. Devices according to some embodiments of the present invention can be implanted using minimally invasive techniques due to the fabric being able to undergo compression under application of a force from a catheter or handling device (such as forceps) and upon removal of such force return to its original dimensions. By returning to its original dimensions the device can be implanted that fulfills the shape, structure, and dimensions of the damaged tissue to be replaced.

Removal of damaged tissues such as arthritic cartilage involves removal of diseased and damaged tissues by debriding the tissue to the subchondral bone. As shown in FIGS. 36-41, this process can occur on the femoral head (910) of a patient, the damaged tissue (911) is located and is removed using debridement leaving a device implant site (912). In some embodiments, the femoral head (930) will also have tissue damage (931) of the bone beneath articular cartilage and the debridement will include all damaged tissues leaving a deeper recess or device implant site (932). In this case, the subchondral bone beneath the cartilage will need to be removed if damaged. Upon removal of the damaged tissues a recess (932) is formed and measured using a scaled surgical device to identify the correct size for the device (920). To treat defects occurring within the femoral condyles, for example, four holes are drilled equidistant in the underlying bone. Sutures can be attached on the fabric fixation points of the second fabric and are guided through the holes using firm action to provide tension to position the device into the defect. Different color sutures can be utilized to assist with device positioning. Following the attachment of the second fabric to the underlying bone, the first fabric is sutured to the surrounding cartilage to create a tight seal integrating the first fabric with the surrounding cartilage. Tensioning of the second fabric following suturing of the first fabric can provide maximum tension on the device in order to ensure separation of the first and second fabrics. Separation of the first and second fabrics will place the plurality of spacer elements under tension which will maximize the compressive resistance of the device. Based on the construction of the first fabric, suturing to the surrounding cartilage provides in-plane tension for the fabric while the fabric fixation points in the second fabric provide downward (boneward) tension, anchoring the device in place.

In some embodiments of device (900), the damaged tissues reside within the femoral condyles of the patient and would be identified using medical imaging technologies. The damaged tissue would be removed via debridement to yield a device implant site (912) and the device (900) would be surgically implanted and secured in the device implant site (912). In some embodiments the device can be secured according to any suitable method including sutures, staples, screws, tethers, or a combination thereof. The device can include fabric fixation points from the second fabric (905) that are affixed through a trans-osseos tunnel (908) via sutures (906) and adhered through cortical bone (910). The benefits of the fabric fixation points (907) include reduced stress concentration on specific points of the first fabric (901). Some embodiments utilize fabric fixation points (907) that are in fact part of the first fabric (901) of the device (900). The fabric fixation points (907), in some cases, would provide a superior tensioning mechanism by increasing the area of the device under tension, lowering potential stress concentrations that could occur via individual sutures attached to specific portions of the device. Additionally, the first fabric (901) can be sutured to the surrounding cartilage to provide in-plane tension to the first fabric (901) to enhance the shear and frictional properties as well as provide dual fixation mechanism for the device (900). In another embodiment for replacing articular cartilage, it may be determined that the underlying bone is also damaged (931). A similar procedure would take place where the damaged tissue (931) is removed leaving a device implant site (932), and a device (920) comprising two devices joined together where the first device is for the regeneration of cartilage and is comprised of a first fabric (921), a second fabric, and a first plurality of spacer elements. The second device is for the regeneration of bone and is comprised of a third fabric, a fourth fabric and a second plurality of spacer elements and is surgically implanted at the defect site (900). The two devices are adjoined at the second and third fabrics using means such as sutures, tabs, tissue adhesives or any other practiced means. The adjoined devices at the second and third fabric create two separate interfabric spaces between the first and second fabric as well as between the third and fourth fabric which can be loaded with different biologically active materials. The adjoining of the second fabric of the first device with the third fabric of the second device yields a continuous approximately planar interface creating a thick fabric interface between the first and the second devices. The device can also include fabric fixation points (925) from the fourth fabric of the bone component of the device that are affixed through a trans-osseos tunnel (928) via sutures (926) and adhered through cortical bone (930). The first fabric (921) of the cartilage region can be affixed to the surrounding tissue to provide in-plane tension to enhance the shear and frictional properties of the first fabric (921) as well as provide a second fixation mechanism (927) for the device.

The benefit of some of the devices of the present invention is that it 1) provides two means of attachment where the second fabric (the fabric adjacent to the subchondral bone) is anchored in place through trans-osseous sutures. The second adhesion mechanism will be provided by suturing the device where the first fabric is anchored in place through at least one suture to the surrounding healthy cartilage and can feature a fabric overlap of the first fabric. This suture will place the first fabric under in-plane tension to which will further provide a smooth surface for articulation as well as attachment to the tissue. Based on the second fabric being adhered to the underlying bone and the first fabric being adhered to the surrounding healthy cartilage, the plurality of spacer elements may be in direct contact with the surrounding healthy cartilage and allow outgrowth of cartilage from the device to integrate with healthy cartilage, or vice versa. As shown in FIGS. 36-41, the first fabric (921) can feature a fabric overlap (927) where the outer edge is devoid of the plurality of spacer elements and it can be configured to overlap the surrounding cartilage or other healthy tissue.

In some embodiments of the present invention, the device can be designed for meniscus replacement. For example, the device can be adapted with external insertion points to achieve fixation when inserted into surgically-drilled holes in the tibia. The device for meniscal regeneration can feature a short anterior fabric fixation point and a longer posterior fabric fixation point. The fabric fixation points are comprised of both the first and the second fabric with the removal or collapse of the plurality of spacer elements. The fabric fixation points are then anchored to the bone, either through pre-drilled tunnels or to nearby tissue, via the addition of sutures to the fabrics. By minimizing the thickness of the device at the fabric fixation point, we can provide maximum tensile strength due to a reduction in the cross-sectional area of the device. The fabric fixation points can be fastened by any means such as a screw mechanism that penetrates through the fabrics through a suitable hole. The posterior fabric fixation point can utilize an insertion threaded through the tibia to place the device under tension. In some embodiments of the device, it may be applicable to replace the underlying tissues of the meniscus such as the bone of the tibial plateau to which the meniscus is attached, too. In this embodiment the c-shaped meniscus replacement device is employed with a second device for the replacement of bone tissue.

In certain embodiments of this invention, the devices are sterile or are sterilized following construction and prior to implantation by any suitable sterilization methods, including ethylene oxide, gamma irradiation, beta irradiation, steam autoclaving, or any other practiced method. In some embodiments the device can be generated from any suitable materials. In some embodiments, the device can include biodegradable, non-degradable, natural, and synthetic materials, and combinations thereof. In some embodiments, all materials used in the device construction are biocompatible, non-cytotoxic, non-irritating, non-toxic, non-pyrogenic, non-mutagenic, non-antigenic, or non-hemolytic, or a combination thereof. Synthetic biodegradable materials are chosen based on their ability to degrade over time due to hydrolytic or enzymatic degradation mechanisms and include, but are not limited to, poly(lactic acid), poly (glycolic acid), poly(caprolactone), poly(sebacate), poly(glycerol), poly(octanediol-co-citrate), poly(urethane), polydioxane, poly(glutamic acid) and any copolymers thereof. The device can also be fabricated from non-degradable polymers including poly(ethylene), ultra-high molecular weight poly (ethylene), polypropylene, poly(ethylene terephthalate), poly(ether etherketones), and nylon, and combinations thereof. Additionally or alternatively, the device can include one or more natural biopolymers including but not limited to silk, cellulose, alginate, hyaluronan, and collagen. In some embodiments, the device can be constructed from a combination of degradable, non-degradable, and/or natural biopolymers. For instance in device (100), fabrics (101 and 103) can be constructed from poly(ethylene terephthalate), while the plurality of spacer elements (102) are constructed from poly(lactic acid). In another example in device (100), first fabric (101) can be constructed from poly(caprolactone), second fabric (103) can be constructed from poly(lactic acid), and the plurality of spacer elements (102) can be constructed from poly(ethylene terephthalate).

In some embodiments, the device can undergo additional processing methods to enhance the end function of the device. This can include, but is not limited to, napping, shearing, heat treatment, yarn treatment prior to fabric construction and is known to those skilled in the art.

EMBODIMENTS OF INVENTION

Embodiment 1

An implantable device for the replacement or repair of musculoskeletal tissue, comprising:
a first fabric,
a second fabric,
and a plurality of spacer elements connecting the first fabric to the second fabric, wherein the first fabric and the second fabric define an interfabric space.

Embodiment 2

The implantable device of embodiment 1, wherein the first fabric and second fabric are substantially planar and substantially parallel.

Embodiment 3

The implantable device of any of embodiments 1-2, wherein the first fabric, the second fabric, or both, are formed by weaving, knitting, or a combination thereof.

Embodiment 4

The implantable device of any of embodiments 1-3, wherein the first fabric, the second fabric, or both, are formed by weft knitting.

Embodiment 5

The implantable device of any of embodiments 1-4, wherein the first fabric, the second fabric, or both, are formed by warp knitting.

Embodiment 6

The implantable device of any of embodiments 1-5, wherein the plurality of spacer elements occupies from about 10% to about 80% by volume of the interfabric space.

Embodiment 7

The implantable device of any of embodiments 1-6, wherein the plurality of spacer elements occupies from about 20% to about 50% by volume of the interfabric space.

Embodiment 8

The implantable device of any of embodiments 1-7, wherein the plurality of spacer elements occupies from about 30% to about 80% by volume of the interfabric space.

Embodiment 9

The implantable device of any of embodiments 1-8, wherein the plurality of spacer elements separates the first fabric from the second fabric a distance ranging from about 1 mm to about 10 mm in an uncompressed state.

Embodiment 10

The implantable device of any of embodiments 1-9, wherein the plurality of spacer elements separates the first fabric from the second fabric a distance ranging from about 2 mm to about 6 mm in an uncompressed state.

Embodiment 11

The implantable device of any of embodiments 1-10, comprising a first fabric, a second fabric, and a plurality of spacer elements, or a combination thereof, comprised of a mono-filament yarn, a multi-filament yarn, or a combination thereof.

Embodiment 12

The implantable device of any of embodiments 1-11, wherein
the first fabric comprises a multi-filament yarn,
the second fabric comprises a multi-filament yarn that is alike or different from the multi-filament yarn of the first fabric, and
the plurality of spacer elements comprise a mono-filament yarn.

Embodiment 13

The implantable device of any of embodiments 1-12, wherein the first fabric is formed from a multi-filament yarn having a denier ranging from about 20 to about 70 denier with a filament count ranging from about 18 to about 96 per yarn.

Embodiment 14

The implantable device of any of embodiments 1-13, wherein the second fabric is formed from yarn of higher denier and lower filament count respective to the first fabric ranging from about 20 to about 160 denier with filament counts ranging from about 18 to about 44 filaments per yarn.

Embodiment 15

The implantable device of any of embodiments 1-14, wherein the first fabric and second fabric are constructed from different yarn feeder run in lengths.

Embodiment 16

The implantable device of any of embodiments 1-15, wherein the first fabric exhibits a higher stitch density than the second fabric.

Embodiment 17

The implantable device of any of embodiments 1-16, wherein the first fabric exhibits a porosity that is lower than the porosity exhibited by the second fabric.

Embodiment 18

The implantable device of any of embodiments 1-17, wherein the second fabric comprises one or more fixation points.

Embodiment 19

The implantable device of any of embodiments 1-18, wherein the one or more fixation points are integrally attached to the second fabric.

Embodiment 20

The implantable device of embodiment 19, wherein at least one fixation point is an extension of the second fabric.

Embodiment 21

The implantable device of any of embodiments 1-20, wherein the first fabric comprises an overlap of 1-5 mm greater than the region of the first fabric comprising the plurality of spacer elements.

Embodiment 22

The implantable device of any of embodiments 1-21, wherein the first fabric comprises one or more fixation points.

Embodiment 23

The implantable device of embodiment 22, wherein the one or more fixation points are integrally attached to the first fabric.

Embodiment 24

The implantable device of embodiment 22, wherein at least one fixation point is an extension of the first fabric.

Embodiment 25

The implantable device of any of embodiments 1-24, wherein the second fabric comprises an overlap of 1-10 mm greater than the region of the second fabric comprising the plurality of spacer elements.

Embodiment 26

The implantable device of any of embodiments 1-25, wherein the device is adapted to replace or repair a damaged meniscus of a patient.

Embodiment 27

The implantable device of any of embodiments 1-26, wherein the first fabric and the second fabric are joined for a portion of the perimeter of the device.

Embodiment 28

The implantable device of any of embodiments 1-27, wherein the interfabric space differs in thickness in one portion of the device from another portion of the device.

Embodiment 29

The implantable device of any of embodiments 1-28 wherein the device comprises an anterior attachment.

Embodiment 30

The implantable device of any of embodiments 1-29, wherein the anterior attachment comprises an extension of the first fabric, the second fabric, or a combination of the first fabric and the second fabric.

Embodiment 31

The implantable device of any of embodiments 29-30, wherein the anterior attachment defines a hole for attachment of a screw mechanism to surrounding tissue.

Embodiment 32

The implantable device of any of embodiments 29-31, wherein the anterior attachment has a length ranging from about 10 to about 200 mm.

Embodiment 33

The implantable device of any of embodiments 1-32, further comprising a posterior attachment.

Embodiment 34

The implantable device of embodiment 33, wherein the posterior attachment comprises an extension of the first fabric, the second fabric, or a combination of the first fabric and the second fabric.

Embodiment 35

The implantable device of any of embodiments 32-33, wherein the posterior attachment has a length ranging from about 30 to about 400 mm.

Embodiment 36

The implantable device of any of embodiments 1-35, wherein the first fabric comprises a material not present in the second fabric.

Embodiment 37

The implantable device of any of embodiments 1-36, exhibiting a stiffness ranging from about 0.01 MPa to about 2 MPa along an axis normal to a point on the first fabric.

Embodiment 38

The implantable device of any of embodiments 1-37, exhibiting a stiffness ranging from about 0.05 MPa to about 2 MPa along an axis normal to a point on the first fabric.

Embodiment 39

The implantable device of any of embodiments 1-37, exhibiting a stiffness ranging from about 0.1 MPa to about 1.2 MPa along an axis normal to a point on the first fabric.

Embodiment 40

The implantable device of any of embodiments 1-37, exhibiting a stiffness ranging from about 0.01 MPa to about 0.3 MPa along an axis normal to a point on the first fabric.

Embodiment 41

The implantable device of any of embodiments 1-37, exhibiting a stiffness ranging from about 0.1 MPa to about 0.2 MPa along an axis normal to a point on the first fabric.

Embodiment 42

The implantable device of any of embodiments 1-37, exhibiting a stiffness ranging from about 1 MPa to about 2 MPa along an axis normal to a point on the first fabric.

Embodiment 43

The implantable device of any of embodiments 1-37, exhibiting a stiffness ranging from about 1.5 MPa to about 2 MPa along an axis normal to a point on the first fabric.

Embodiment 44

The implantable device of any of embodiments 1-43, having a thickness in an uncompressed state, and exhibiting a return to at least 95% of that thickness within one minute upon removal of a compressive force ranging from about 1 to about 12 MPa.

Embodiment 45

The implantable device of any of embodiments 1-44, wherein the first fabric exhibits a tensile modulus ranging from about 10 MPa to about 300 MPa in either in the x direction or in the y direction as being substantially planar.

Embodiment 46

The implantable device of any of embodiments 1-44, wherein the first fabric exhibits a tensile modulus ranging from about 10 MPa to about 30 MPa in either tin the x direction or in the y direction as being substantially planar.

Embodiment 47

The implantable device of any of embodiments 1-44, wherein the first fabric exhibits a tensile modulus ranging from about 25 MPa to about 30 MPa in either in the x direction or in the y direction as being substantially planar.

Embodiment 48

The implantable device of any of embodiments 1-44, wherein the first fabric exhibits a tensile modulus ranging from about 100 MPa to about 300 MPa in either the x direction or in the y direction as being substantially planar.

Embodiment 49

The implantable device of any of embodiments 1-44, wherein the first fabric exhibits a tensile modulus ranging from about 200 MPa to about 300 MPa in either in the x direction or in the y direction as being substantially planar.

Embodiment 50

The implantable device of any of embodiments 1-42, wherein the first fabric exhibits a tensile modulus ranging from about 250 MPa to about 300 MPa in either in the x direction or in the y direction as being substantially planar.

Embodiment 51

The implantable device of any of embodiments 1-50, wherein the second fabric exhibits a tensile modulus ranging from about 1 MPa to about 300 MPa in either in the x direction or in the y direction as being substantially planar.

Embodiment 52

The implantable device of any of embodiments 1-51, wherein the first fabric and the second fabric exhibit tensile moduli that are substantially equal in either in the x direction or in the y direction as being substantially planar.

Embodiment 53

The implantable device of embodiment 52, wherein the tensile moduli range from about 1 MPa to about 30 MPa in either in the x direction or in the y direction as being substantially planar.

Embodiment 54

The implantable device of embodiment 52, wherein the tensile moduli range from about 10 MPa to about 300 MPa in either in the x direction or in the y direction as being substantially planar.

Embodiment 55

The implantable device of any of embodiments 1-54, wherein at least one biologically active material is present in the interfabric space.

Embodiment 56

The implantable device of embodiment 55, wherein the at least one biologically active material is chosen from peptides, proteins, cells, tissues, and combinations thereof.

Embodiment 57

The implantable device of any of embodiments 55-56, wherein the at least one biologically active material is derived from an autogenic source.

Embodiment 58

The implantable device of any of embodiments 55-56, wherein the at least one biologically active material is derived from an allogenic source.

Embodiment 59

The implantable device of any of embodiments 55-56, where in the at least one biologically active material is derived from a xenogenic source.

Embodiment 60

The implantable device of any of embodiments 55-56, where in the at least one biologically active material is derived from a synthetic source.

Embodiment 61

The implantable device of any of embodiments 55-60, wherein the at least one biologically active material is chosen from cartilage tissue, meniscal tissue, bone tissue, bone marrow aspirate, adipose tissue aspirate, and combinations thereof.

Embodiment 62

The implantable device of any of embodiments 55-61, wherein the at least one biologically active material is chosen from chondrocytes, fibroblasts, mesenchymal stem cells, osteoblasts, osteocytes, fibrochondrocytes of allogenic, autologous, or xenogenic source and combinations thereof.

Embodiment 63

The implantable device of any of embodiments 55-62, wherein the at least one biologically active material comprises at least one hydrogel.

Embodiment 64

The implantable device of embodiment 63, wherein the at least one hydrogel is chosen from alginate, hyaluronic acid, collagen, chondroitin sulfate, polyethylene glycol, agarose, fibrin, and combinations thereof.

Embodiment 65

The implantable device of any of embodiments 1-64, adapted to allow lateral outgrowth of cells present in the interfabric space.

Embodiment 66

The implantable device of any of embodiments 1-65, adapted to allow the lateral ingrowth of native tissue into the interfabric space.

Embodiment 67

The implantable device of any of embodiments 1-66, wherein the plurality of spacer elements comprises a material not present in the first fabric or the second fabric.

Embodiment 68

The implantable device of any of embodiments 1-67, wherein at least a portion of the first fabric, at least a portion of the second fabric, and at least a portion of the plurality of spacer elements comprise the same material.

Embodiment 69

The implantable device of any of embodiments 1-68, comprising a non-biodegradable material chosen from: poly (ethylene), ultra-high molecular weight poly(ethylene), polypropylene, poly(ethylene terephthalate), poly(ether etherketones), nylon, copolymers of two or more thereof, and combinations thereof.

Embodiment 70

The implantable device of any of embodiments 1-69, comprising a biodegradable material chosen from: poly (lactic acid), poly (glycolic acid), poly(caprolactone), poly (sebacate), poly(glycerol), poly(octanediol-co-citrate), poly (urethane), polydioxane, poly(glutamic acid), copolymers of two or more thereof, and combinations thereof.

Embodiment 71

The implantable device of any of embodiments 1-70, comprising at least one non-biodegradable material and at least one biodegradable material.

Embodiment 72

The implantable device of any of embodiments 1-71, comprising: silk, cellulose, alginate, chitosan, hyaluronan, collagen, or a combination of two or more thereof.

Embodiment 73

The implantable device of any of embodiments 1-72, further comprising at least one inorganic component.

Embodiment 74

The implantable device of embodiment 73, wherein the at least one inorganic component is chosen from calcium salts, bioactive glasses, and combinations thereof.

Embodiment 75

The implantable device of any of embodiments 73-74, wherein the at least one inorganic component comprises at least one calcium salt chosen from calcium chloride, calcium carbonate, α-tricalcium phosphate, β-tricalcium phosphate, hydroxyapatite, and combinations thereof.

Embodiment 76

The implantable device of any of embodiments 73-75, wherein the at least one inorganic component comprises at least one bioactive glass comprising silica, calcium, strontium, cobalt, barium, or a combination thereof.

Embodiment 77

The implantable device of any of embodiments 1-76, wherein the device comprises:
a first fabric,
a second fabric,
a first plurality of spacer elements between the first fabric and the second fabric,
a third fabric,
a fourth fabric,
a second plurality of spacer elements between the third and fourth fabric
wherein the second and third fabric are adjoined, forming a first interfabric space between the first fabric and second fabric, and a second interfabric space between the third fabric and the fourth fabric.

Embodiment 78

The implantable device of any of embodiments 1-77, wherein the device is adapted to repair a tissue interface exhibiting an osteochondral tissue defect.

Embodiment 79

A method of repairing or replacing musculoskeletal tissue in a human or animal patient in need thereof, comprising:
implanting into the patient the implantable device of any of embodiments 1-78, thereby repairing or replacing the musculoskeletal tissue.

Embodiment 80

The method of embodiment 79, further comprising:
removing at least a portion of the musculoskeletal tissue to be replaced or repaired.

Embodiment 81

The method of embodiment 80, wherein the removing comprises debriding at least some of the portion of the musculoskeletal tissue to be replaced or repaired.

Embodiment 82

The method of any of embodiments 79-81 further comprising:
measuring a dimension of a defect of the musculoskeletal tissue to be replaced or repaired using a scaled surgical device, and
determining a dimension of the device from the dimension of the defect.

Embodiment 83

The method of any of embodiments 79-82, further comprising:
drilling one or more holes through a bone and surrounding tissues of the patient for placement of the device.

Embodiment 84

The method of any of embodiments 79-83, wherein the device further comprises one or more device fixation points protruding from the second fabric, the method further comprising:
attaching a suture to a device fixation point,
guiding the device fixation point into one of the holes drilled through the bone using the suture, and attaching the suture to the bone distal to the device, and
optionally tensioning the device fixation point.

Embodiment 85

The method of any of embodiments 79-84, wherein the first fabric comprises an overlap protruding from the first fabric, the method further comprising: attaching the overlap to adjacent healthy tissue.

Embodiment 86

A method of making an implantable device of any of embodiments 1-78 for the replacement or repair of musculoskeletal tissue, comprising:
forming a first fabric, a second fabric, and a plurality of spacer elements connecting the first fabric to the second fabric, wherein the first fabric and the second fabric define an interfabric space; and
inserting into the interfabric space at least one biologically active material.

Embodiment 87

A method of making the implantable device of any of embodiments 1-78 for the replacement or repair of musculoskeletal tissue, comprising:
forming a first fabric, a second fabric, and a plurality of spacer elements connecting the first fabric to the second fabric, wherein the first fabric and the second fabric define an interfabric space;
removing or disconnecting one or more spacer elements to change at least one property of the implantable device.

Detailed embodiments of the present invention are disclosed herein. However, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one." "About" is intended to be construed as having a reasonable scope as would be given by one of ordinary skill in the art.

The invention claimed is:

1. An implantable device for the replacement or repair of a damaged meniscus of a patient, comprising:
   a first fabric adapted for articulation against a tissue within a human or animal body,
   a second fabric adapted for tissue ingrowth within a human or animal body,
   a first plurality of spacer elements connecting the first fabric to the second fabric,
   wherein the first plurality of spacer elements separates the first fabric from the second fabric,
   and creates a first interfabric space between the first fabric and the second fabric, and
   at least one first fabric fixation point provided by the first fabric, the second fabric, or both, and a third fabric, a fourth fabric, and a second plurality of spacer elements connecting the third fabric to the fourth fabric and creating a second interfabric space between the third fabric and the fourth fabric, and at least one second fabric fixation point provided by the third fabric, the fourth fabric, or both;

wherein the second fabric and the third fabric are adjoined;

wherein the at least one second fabric fixation point is adapted to anchor the implantable device in bone tissue.

2. The implantable device of claim 1, wherein the first plurality of spacer elements provides compressive stiffness ranging from 0.1 MPa to 1.2 MPa along an axis normal to a point on the first fabric.

3. The implantable device of claim 1, comprising at least one non-biodegradable material comprising: poly(ethylene), ultra-high molecular weight poly(ethylene), polypropylene, poly(ethylene terephthalate), poly(ether etherketones), nylon, copolymers of two or more thereof, and combinations thereof.

4. The implantable device of claim 1, further comprising at least one inorganic component.

5. The implantable device of claim 4, wherein the at least one inorganic component is chosen from calcium salts, bioactive glasses, and combinations thereof.

6. The implantable device of claim 4, wherein the at least one inorganic component comprises at least one calcium salt chosen from calcium chloride, calcium carbonate, α-tricalcium phosphate, β-tricalcium phosphate, hydroxyapatite, and combinations thereof.

7. The implantable device of claim 4, wherein the at least one inorganic component comprises at least one bioactive glass comprising silica, calcium, strontium, cobalt, barium, or a combination thereof.

8. The implantable device of claim 1, wherein the first plurality of spacer elements separates the first fabric from the second fabric a distance ranging from about 2 mm to about 6 mm in an uncompressed state.

9. The implantable device of claim 1, comprising a mono-filament yarn, a multi-filament yarn, or a combination thereof.

10. The implantable device of claim 1, wherein
the first fabric comprises a multi-filament yarn,
the second fabric comprises a multi-filament yarn that is alike or different from the multi-filament yarn of the first fabric, and
the first plurality of spacer elements comprises a mono-filament yarn.

11. The implantable device of claim 1, wherein the first fabric is formed from a multi-filament yarn having a denier ranging from about 20 to about 70 denier with a filament count ranging from about 18 to about 96 per yarn.

12. The implantable device of claim 1, wherein the second fabric is formed from yarn of higher denier and lower filament count respective to the first fabric ranging from about 20 to about 160 denier with filament counts ranging from about 18 to about 44 filaments per yarn.

13. The implantable device of claim 1, wherein the first fabric and second fabric are constructed from different yarn feeder run in lengths.

14. The implantable device of claim 1, wherein the first fabric comprises an overlap of 1-5 mm greater than the region of the first fabric comprising the plurality of spacer elements.

15. The implantable device of claim 1, wherein the at least one first fabric fixation point is integrally attached to the first fabric.

16. The implantable device of claim 1, wherein the at least one first fabric fixation point is an extension of the first fabric.

17. The implantable device of claim 1, wherein the second fabric and third fabric are adjoined by suturing, laminating, thermal bonding, or any combination thereof.

18. The implantable device of claim 1, wherein the second plurality of spacer elements provides a greater compressive stiffness than the first plurality of spacer elements.

19. The implantable device of claim 1, wherein at least one biologically active material is loaded into the first interfabric space, the second interfabric space, or both.

20. The implantable device of claim 19, wherein the at least one biologically active material comprises a first biologically active material loaded into the first interfabric space, and a second biologically active material loaded into second interfabric space;

wherein the first biologically active material and the second biologically active material are different.

* * * * *